(12) United States Patent
Brack et al.

(10) Patent No.: US 9,085,760 B2
(45) Date of Patent: Jul. 21, 2015

(54) CHYMASE BINDING COMPOUNDS AND MEDICAL USES THEREOF

(75) Inventors: Simon Brack, Winterthur (CH); Sarah Batey, Derrington (GB); Dragan Grabulovski, Zurich (CH); Julian Bertschinger, Hombrechtikon (CH); Daniel Schlatter, Ettingen (CH); Jörg Benz, Rheinfelden (DE); David Banner, Basel (CH); Michael Hennig, Weil am Rhein (DE)

(73) Assignee: COVAGEN AG, Zurich-Schlieren (CH)

( * ) Notice: Subject to any disclaimer, the term of this patent is extended or adjusted under 35 U.S.C. 154(b) by 0 days.

(21) Appl. No.: 14/119,002

(22) PCT Filed: Apr. 24, 2012

(86) PCT No.: PCT/EP2012/057489
§ 371 (c)(1),
(2), (4) Date: Dec. 31, 2013

(87) PCT Pub. No.: WO2012/159836
PCT Pub. Date: Nov. 29, 2012

(65) Prior Publication Data
US 2014/0162936 A1   Jun. 12, 2014

(30) Foreign Application Priority Data

May 20, 2011   (EP) .................................... 11004180

(51) Int. Cl.
| *A61K 38/16* | (2006.01) |
| *C07K 14/00* | (2006.01) |
| *C12N 9/12* | (2006.01) |
| *C07K 14/47* | (2006.01) |
| *G01N 33/573* | (2006.01) |

(52) U.S. Cl.
CPC .............. *C12N 9/12* (2013.01); *C07K 14/4703* (2013.01); *C12N 9/1205* (2013.01); *G01N 33/573* (2013.01)

(58) Field of Classification Search
CPC .... C07K 14/4703; G01N 33/573; C12N 9/12; C12N 9/1205
See application file for complete search history.

(56) References Cited

FOREIGN PATENT DOCUMENTS

WO   WO 2011/023685   3/2011

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Sequence listing of WO 2011/023685 A1, pp. 1-69, published on Mar. 3, 2011.*
Brown et al, Angiotensin-Converting Enzyme Inhibitors, Circulation, 1998, 97, pp. 1411-1420.*

* cited by examiner

*Primary Examiner* — Julie Ha
*Assistant Examiner* — Li Ni Komatsu
(74) *Attorney, Agent, or Firm* — Hunton & Williams LLP

(57) ABSTRACT

The present invention relates to a polypeptide binding to a chymase (EC 3.4.21.39), wherein the polypeptide comprises or consists of an amino acid sequence selected from the group consisting of: (a) GVTLFVALYDY($X^1$)A($X^2$)($X^3$)($X^4$)($X^5$) ($X^6$)LSFHKGEKFQIL($X^7$)($X^8$)($X^9$)($X^{10}$) ($X^{11}$)($X^{12}$)G ($X^{13}$)($X^{14}$)WEARSLTTGETGYIPSNYVAPVDSIQ (SEQ ID NO: 1), wherein ($X^1$) is R, N, Q, E, K, H, S, T, C, or D; ($X^2$) is E, T, D, Q, L, P, A, S, C, M, N, E, G, A, V or I; ($X^3$) is R, T, H, N, K, S, C, N or Q; ($X^4$) is S, W, T, C, N, Q, F or Y; ($X^5$) is T, H, L, F, C, S, M, N, Q, R, K, G, A, V, I, P, Y or W; ($X^6$) is D, Q, H, E, S, T, C, N, R or K; ($X^7$) is D, N, R, E, Q, S, T, C, K or D; ($X^8$) is M, W, G, F, A, T, C, S, N, Q, Y, V, L, I or P; ($X^9$) is T, H, S, D, C, N, Q, R, K, E or absent; ($X^{10}$) is V, T, Q, G, A, L, I, P, S, C, M, N or absent; ($X^{11}$) is P, A, D, G, K, V, L, I, E, R, M, H or absent; ($X^{12}$) is N, V, P, I, E, T, S, A, G, L, C, M, Q or D; ($X^{13}$) is D, E, T, P, G, A, V, L, I, S, C, M, N or Q, and ($X^{14}$) is W, Y, L, G, A, V, I, P, M, or F; (b) an amino acid sequence which is at least 85% identical to the amino acid sequence of (a), wherein the identity determination excludes amino acid positions ($X^1$) to ($X^{14}$).

8 Claims, 7 Drawing Sheets
(3 of 7 Drawing Sheet(s) Filed in Color)

|  | | 10 | 20 | 30 | 40 |
|---|---|---|---|---|---|
| SEQ ID NO: | 2 | GVTLFVALYD | YRAERSTDLS | FHKGEKFQIL | DMTVPNGDWW |
| SEQ ID NO: | 3 | GVTLFVALYD | YNATRWTDLS | FHKGEKFQIL | DWTTANGDWW |
| SEQ ID NO: | 4 | GVTLFVALYD | YNATRWTDLS | FHKGEKFQIL | DG--DSGDWW |
| SEQ ID NO: | 5 | GVTLFVALYD | YQADRWTDLS | FHKGEKFQIL | SFH--VGDWW |
| SEQ ID NO: | 6 | GVTLFVALYD | YQADRWTDLS | FHKGEKFQIL | NAS-GPGDWW |
| SEQ ID NO: | 7 | GVTLFVALYD | YQADRWTDLS | FHKGEKFQIL | RFD--IGDWW |
| SEQ ID NO: | 8 | GVTLFVALYD | YQADRWTDLS | FHKGEKFQIL | DAS-PPGDWW |
| SEQ ID NO: | 9 | GVTLFVALYD | YNATRWTDLS | FHKGEKFQIL | EF--GPGDWW |
| SEQ ID NO: | 10 | GVTLFVALYD | YEAQTWHDLS | FHKGEKFQIL | NSS--EGEYW |
| SEQ ID NO: | 11 | GVTLFVALYD | YKAQRWTDLS | FHKGEKFQIL | QAHQKTGDWW |
| SEQ ID NO: | 12 | GVTLFVALYD | YEALHWHQLS | FHKGEKSQIL | NSS--EGTYW |
| SEQ ID NO: | 13 | GVTLFVALYD | YKAQRWLDLS | FHKGEKFQIL | STD--SGDWW |
| SEQ ID NO: | 14 | GVTLFVALYD | YEAPTWLHLS | FHKGEKFQIL | NSS--EGPWW |
| SEQ ID NO: | 15 | GVTLFVALYD | YEAANWFQLS | FHKGEKFQIL | NSS--EGPLW |

| 50 | 60 | 65 |
|---|---|---|
| EARSLTTGET | GYIPSNYVAP | VDSIQ |
| EARSLTTGET | GYIPSNYVAP | VDSIQ |
| EARSLTTGET | GYIPSNYVAP | VDSIQ |
| EARSLTTGET | GYIPSNYVAP | VDSIQ |
| EARSLTTGET | GYIPSNYVAP | VDSIQ |
| EARSLTTGET | GYIPSNYVAP | VDSIQ |
| EARSLTTGET | GYIPSNYVAP | VDSIQ |
| EARSLTTGET | GYIPSNYVAP | VDSIQ |
| EARSLTTGET | GLIPSNYVAP | VDSIQ |
| EARSLTTGET | GLIPSNYVAP | VDSIQ |
| EARSLTTGET | GWIPSNYVAP | GDSIQ |
| EARSLTTGET | GYIPSNYVAP | VDSIQ |
| EARSLTTGET | GFIPSNYVAP | VDSIQ |
| EARSLTTGET | GGIPSNYVAP | VDSIQ |

FIG. 1

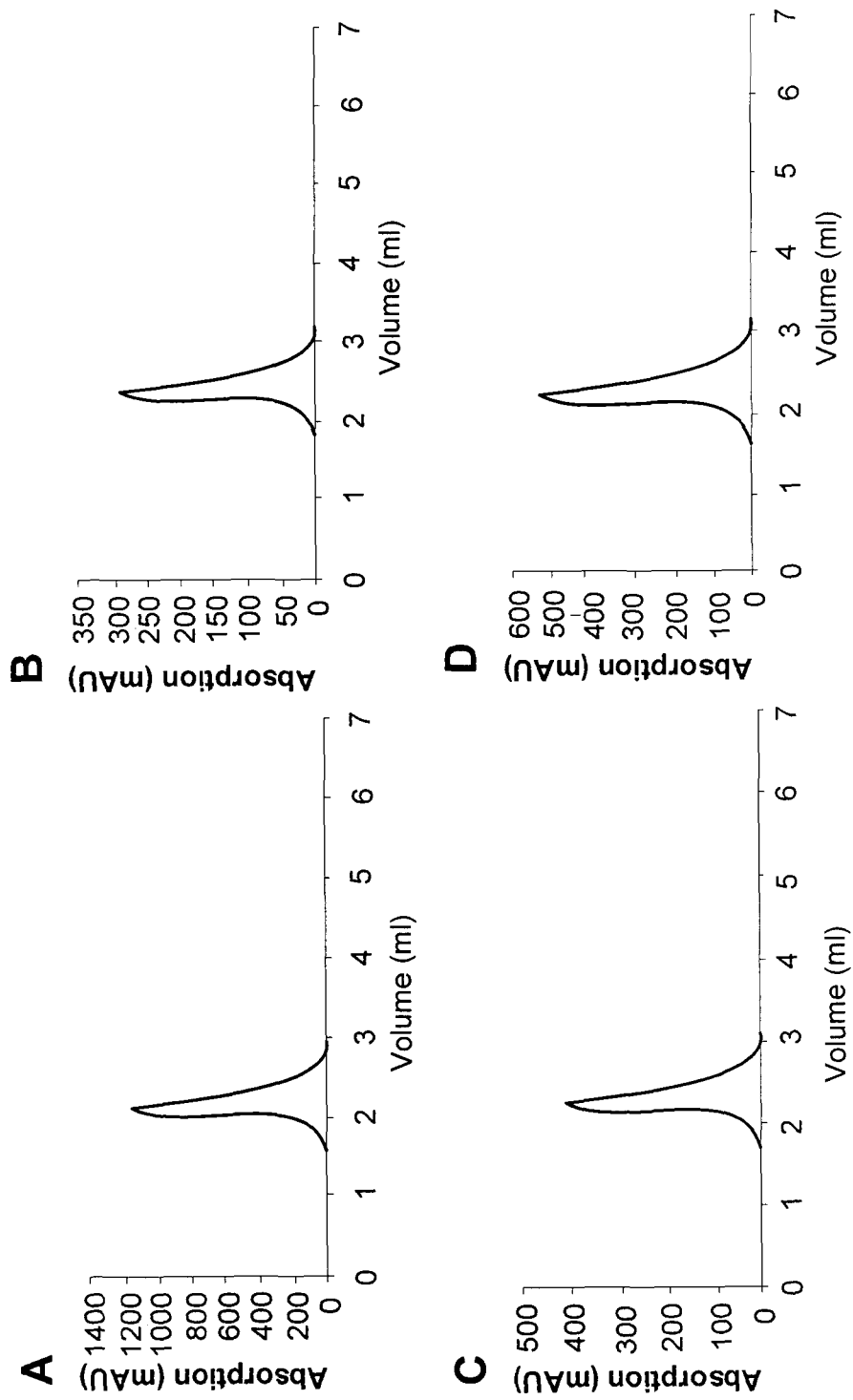
FIG. 3 A-D

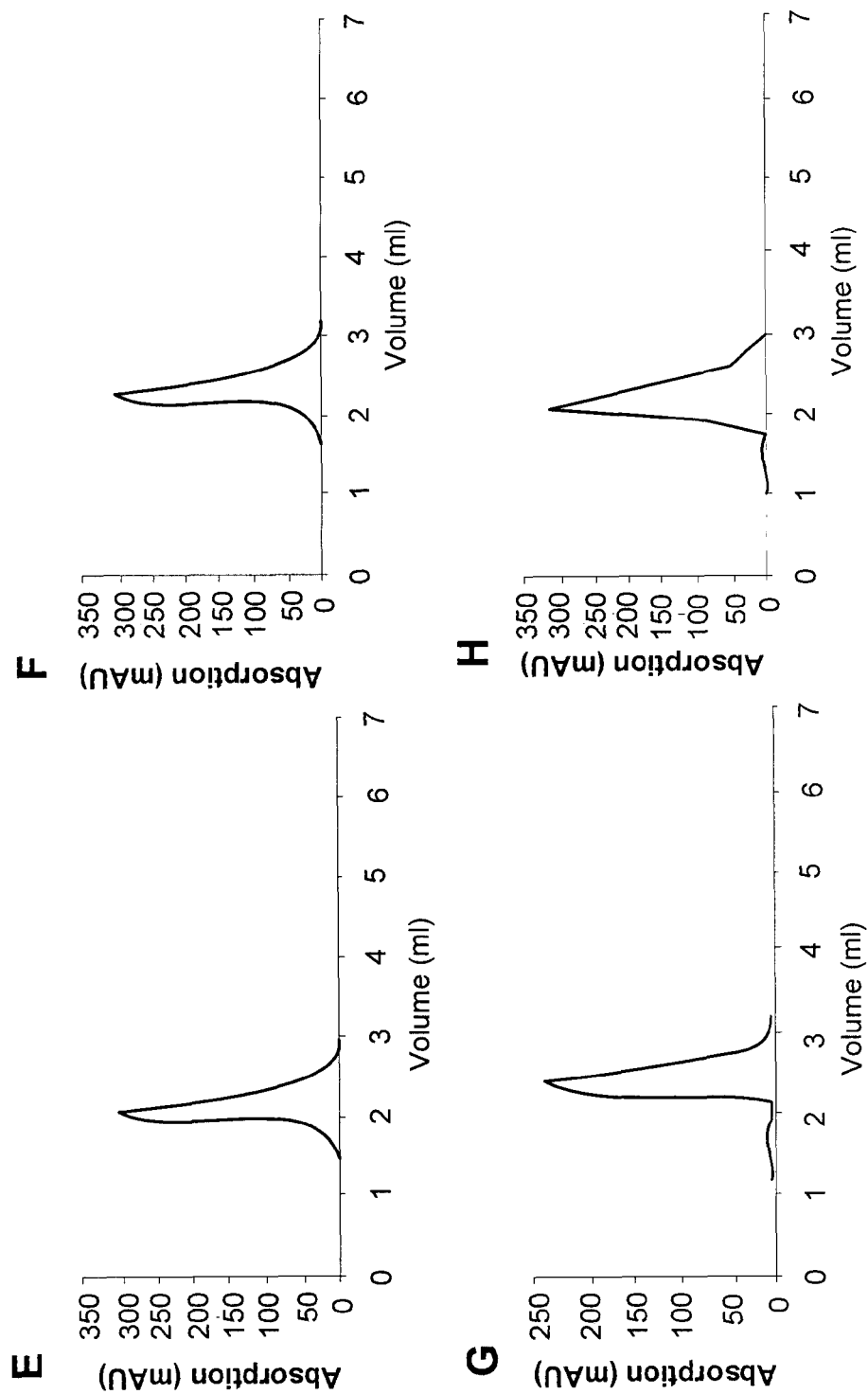
FIG. 3E-H

CHYMASE BINDING COMPOUNDS AND MEDICAL USES THEREOF

CROSS-REFERENCE TO RELATED APPLICATIONS

This patent application is a national stage application of International Patent Application No. PCT/EP2012/057489, filed Apr. 24, 2012, which claims priority to EP Patent Application No. 11004180.3, filed May 20, 2011, the disclosures of each of which are herein incorporated by reference.

FIELD OF THE INVENTION

The present invention relates to a polypeptide binding to a chymase (EC 3.4.21.39), wherein the polypeptide comprises or consists of an amino acid sequence selected from the group consisting of: (a) GVTLFVALYDY($X^1$)A($X^2$)($X^3$)($X^4$)($X^5$) ($X^6$)LSFHKGEKFQIL($X^7$)($X^8$)($X^9$)($X^{10}$) ($X^{11}$)($X^{12}$)G ($X^{13}$)($X^{14}$)WEARSLTTGETGYIPSNYVAPVDSIQ (SEQ ID NO: 1), wherein ($X^1$) is R, N, Q, E, K, H, S, T, C, or D; ($X^2$) is E, T, D, Q, L, P, A, S, C, M, N, E, G, A, V or I; ($X^3$) is R, T, H, N, K, S, C, N or Q; ($X^4$) is S, W, T, C, N, Q, F or Y; ($X^5$) is T, H, L, F, C, S, M, N, Q, R, K, G, A, V, I, P, Y or W; ($X^6$) is D, Q, H, E, S, T, C, N, R or K; ($X^7$) is D, N, R, E, Q, S, T, C, K or D; (X) is M, W, G, F, A, T, C, S, N, Q, Y, V, L, I or P; ($X^9$) is T, H, S, D, C, N, Q, R, K, E or absent; ($X^{10}$) is V, T, Q, G, A, L, I, P, S, C, M, N or absent; ($X^{11}$) is P, A, D, G, K, V, L, I, E, R, M, H or absent; ($X^{12}$) is N, V, P, I, E, T, S, A, G, L, C, M, Q or D; ($X^{13}$) is D, E, T, P, G, A, V, L, I, S, C, M, N or Q, and ($X^{14}$) is W, Y, L, G, A, V, I, P, M or F; (b) an amino acid sequence which is at least 85% identical to the amino acid sequence of (a), wherein the identity determination excludes amino acid positions ($X^1$) to ($X^{14}$).

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

BACKGROUND OF THE INVENTION

In immune-mediated inflammatory diseases, numerous cell types of the immune system, such as neutrophils, monocytes, macrophages, eosinophiles, mast cells and lymphocytes play often a major causative role. The active recruitment and accumulation of these cells are life-saving in some circumstances (e.g., bacterial or nematode infection) but life-threatening in others (e.g., allergy). In particular, mast cells have been considered for many years to participate specifically in allergic reactions through the release of cytokines, chemokines, proteases, leukotrienes, and bioactive polyamines. Emerging roles for mast cells have been identified recently, which highlight their relevance in both innate and adaptive immunity, as well as pathological inflammatory conditions (Shea-Donohue T. et al. (2010), Curr Gastroenterol Rep., 12(5) p. 349-357).

The serine protease chymase (EC=3.4.21.39) is a chymotrypsin-like enzyme that is expressed in the secretory granule of mast cells (Miller H. and Pemberton A., (2002), Immunity, 105, p. 375-390). Upon release, it has been described to degrade the extracellular matrix (e.g., proteoglycans, collagen, elastin, fibronectin), induce leukocyte migration and cytokine production, activate TGF-beta and MMP-9, and promote tissue remodeling (de Garavilla L. et al. (2005) J Biol Chem, 280(18) p. 18001-18007 and Takai S. et al. (2010) J Pharmacol Sci, 113(4), p. 301-309). In addition to these pro-inflammatory effects upon release from the granules of mast cells in different types of tissues, chymase has been found in mast cells in the human heart, where it cleaves angiotensin I to form angiotensin II (Urata et al. (1993) J Clin Invest, 91(4), p. 1269-1281). Angiotensin II in the blood has multiple diverse physiological effects on the cardiovascular system, including arteriolar vasoconstriction and aldosterone secretion. In the heart itself, it has positive inotropic and chronotropic effects (Peach et al. (1977), Physiol. Rev., 57, p. 313-370). In cardiovascular pathologies (such as hypertension), blockade of angiotensin II mediated effects by angiotensin converting enzyme (ACE) inhibitors and angiotensin receptor blockers has shown the usefulness of treating this diseases, as demonstrated by the large number of different marketed compounds (Lüllmann H. and Mohr K., in: Taschenatlas der Pharmakologie, $4^{th}$ edition, Georg Thieme Verlag Stuttgart/New York, 2001, p. 126-127).

Because of the pro-inflammatory enzymatic activities of chymase, and because chymase generates angiotensin II by an ACE-independent pathway in the heart, it has been postulated that inhibition of chymase promises new therapeutic approaches to prevent organ and tissue damage in inflammatory conditions and cardiovascular diseases. According to this rationale, chymase inhibitors have been generated and were investigated as anti-inflammatory and cardioprotective agents in a number of in vivo studies, demonstrating that chymase inhibition reduces inflammatory processes: For example, in initial studies, the inhibition of chymase in an acute peritonitis model in rats reduced the up-regulation of pro-inflammatory cytokines in plasma and/or peritoneum and reduced the influx of neutrophils into the peritoneal cavity (de Garavilla L. et al. (2005) J Biol Chem, 280(18) p. 18001-18007). On the basis of this success, it was investigated whether chymase inhibition is relevant for the treatment of asthma and chronic obstructive pulmonary disease (COPD). Three different animal models of inflammation with pathological responses related to those manifested in allergic asthma and/or COPD were investigated (Maryanoff B. et al. (2010), Am J Respir Crit Care Med, 181 p. 247-253): (1) mast-cell mediated inflammation in ovalbumin sensitized rats, (2) allergen-induced bronchoconstriction and airway hyperresponsiveness in allergic sheep, and (3) tobacco smoke induced neutrophilia in mice. The results presented by the authors indicate that the chymase inhibitor is able to disrupt inflammatory sequelae in animal models associated with diseases related to asthma and COPD (Maryanoff B. et al. (2010), Am J Respir Crit Care Med, 181 p. 247-253). Moreover, a chymase inhibitor prevented vascular proliferation after balloon catheter injury in a dog model (Takai S. et al., (2003), J Pharmacol Exp Ther, 304, p. 841-844). In addition, it was shown that hamsters treated with combined ACE and chymase inhibitors, relative to ACE inhibition alone, improved left ventricular function, decreased adverse cardiac remodelling and improved survival after myocardial infarction. Other animal studies demonstrated efficacy of chymase inhibitors in animal models of myocardial infarction, cardiomyopathy, and tachycardia-induced heart failure (Doggrell Sh. and Wanstall J., (2005), Can J Physiol Pharmacol, 83, p. 123-130). Takai et al. teach that chymase inhibitors may be useful to prevent organ damages in a number of diseases, such as: aortic aneurysm, diabetic retinopathy, fibrosis, ulcerative colitis and other inflammatory disorders (Takai S. et al. (2010) J Pharmacol Sci, 113(4), p. 301-309).

In summary, inhibition of chymase appears a useful modality in inflammatory conditions, in which chymase blockade is desired, such as allergy, asthma, COPD, rheumatoid arthritis, ulcerative colitis, diabetes, Crohn's disease, cardiomyopathy, myocardial infarction, left ventricular hypertrophy, unstable angina pectoris, restenosis and atherosclerotic plaques. Only recently Diaconu et al. (2011), Arch Dermato Res., ahead of print described a role of chymase in cancer, in particular in uterine cervical carcinoma.

In general, the development of compounds that inhibit protease targets (proteases comprise more than 500 family members) with high affinity and specificity has proved challenging in the past. This is reflected by the fact that although proteases are considered as an important target class (because unregulated proteolysis leads to many pathologies, as exemplified above for chymase) it is notable, that there are only few marketed drugs (such as HIV protease inhibitors, angiotensin-converting enzyme (ACE) inhibitors, a kallikrein inhibitor, the proteasome inhibitor bortezomib, the recently approved renin-inhibitor aliskiren, anticoagulation drugs and DPP4-inhibitors). The key challenge in the discovery of new protease inhibitors is the ability to identify drugs which are both potent and specific (Drag M. and Salvesen G., (2010), Nat Rev Drug Discov., 9(9), p. 690-701) as structural similarities within the active site of most proteolytic enzyme families often result in a simultaneous inhibition of several family members, which can lead to an unacceptable toxicity profile of the drug.

One avenue of obtaining high affinity and specific inhibitors of chymase with desired pharmacokinetic and pharmacodynamic properties, represents the use of antibody and alternative binding technologies (the latter termed "scaffolds", see below). Antibodies represent the best established class of binding molecules in the field of pharmaceutical biotechnology. But, even though antibodies are routinely employed for analytical, purification, diagnostic and therapeutic purposes due to their ease of production, high affinity and specificity to virtually any desired target antigen, these still have a number of serious drawbacks such as the necessity of complex mammalian cell production systems, a dependency on disulfide bond for stability, the tendency of some antibody fragments to aggregate, limited solubility and last but not least, they may elicit undesired immune responses even when humanized. As a consequence, a recent focus for developing small globular proteins as scaffolds for the generation of novel classes of versatile binding proteins has emerged. For generating diversity and target specificity, typically surface components (e.g. extracellular loops) of a protein framework with suitable biophysical properties are combinatorially mutated for producing a protein library to be screened for the target binding specificities of interest (Binz, H. K., and Pluckthun, A. (2005) Curr. Opin. Biotechnol. 16, 459-469).

These non-immunoglobulin-derived binding reagents are collectively designated "scaffolds" (Skerra A. (2000) J. Mol. Recognit. 13, 167-187). More than 50 different protein scaffolds have been proposed over the past 10 to 15 years, the most advanced approaches in this field being (as summarized in Gebauer M and Skerra A. (2009) Curr Opinion in Chemical Biology 13:245-255): affibodies (based on the Z-domain of staphylococcal protein A), Kunitz type domains, adnectins (based on the 10th domain of human fibronectin), anticalins (derived from lipocalins), DARPins (derived from ankyrin repeat proteins), avimers (based on multimerized LDLR-A), affitins (based on Sac7d from the hyperthermophilic archaeon), and Fynomers, which are derived from the human Fyn SH3 domain.

In general, SH3 domains are present in a large variety of proteins participating in cellular signal transduction (Musacchio et al. (1994) Prog. Biophys. Mol. Biol. 61; 283-297). These domains do not occupy a fixed position within proteins and can be expressed and purified independently. More than 1000 occurrences of the domain are presently known with about 300 human SH3 domains (Musacchio A. (2003) Advances in Protein Chemistry. 61; 211-268). Although there is great sequence diversity among SH3 domains, they all share a conserved fold: a compact beta barrel formed by two anti-parallel beta-sheets (Musacchio A. (2003) Advances in Protein Chemistry. 61; 211-268). Typically, SH3 domains bind to proline-rich peptides containing a PXXP core-binding motif (Ren et al. (1993) Science 259; 1157-1161), but examples of unconventional SH3 binding sites have also been described (Karkkainen et al. (2006) EMBO Rep. 7; 186-191). Most of the SH3 domains sequenced so far have an overall length of approximately 60 to 65 amino acids, but some of them may feature as many as 85 amino acids due to inserts into the loops connecting the main conservative elements of the secondary structure (Koyama et al. (1993) Cell 72(6); 945-952). An alignment of different SH3 domains revealed conserved amino acid residues responsible for the proper structure formation as well as for the canonical proline-rich motif recognition (Larson et al. (2000) Protein Science 9; 2170-2180).

Recently it was demonstrated that the Fyn SH3 domain is an attractive scaffold ("Fynomer") for the generation of binding proteins because it (i) can be expressed in bacteria in soluble form in high amounts, (ii) is monomeric and does not aggregate when stored in solution, (iii) is very stable (Tm 70.5° C.), (iv) lacks cysteine residues, and (v) is of human origin featuring an amino acid sequence completely conserved from mouse to man and, hence, non-immunogenic (Grabulovski et al. (2007) JBC, 282, p. 3196-3204; EP 2054432).

Whereas chymase is a therapeutically attractive target, to the best knowledge of the inventors, so far no Fynomer-based binders have been described in the art. It was thus challenging to identify and describe features required for binding molecules to chymase that would also provide an impact on their therapeutic applicability.

Thus, the objective underlying the present invention is to provide new potent chymase binding molecules, in particular ones with high specificity and high affinity for chymase. It is a further objective to provide chymase-binding molecules, preferably chymase inhibitors, suitable for research, diagnostic and medical treatment, preferably for use in medicaments for treating and/or preventing chymase-mediated diseases and medical conditions.

SUMMARY OF THE INVENTION

Accordingly, the invention relates in a first embodiment to a polypeptide binding to a chymase (EC 3.4.21.39), wherein the polypeptide comprises or consists of an amino acid sequence selected from the group consisting of: (a) GVTLFVALYDY($X^1$)A($X^2$)($X^3$)($X^4$)($X^5$)($X^6$)LSFHKGE KFQIL($X^7$)($X^8$)($X^9$)($X^{10}$)($X^{11}$)($X^{12}$)G($X^{13}$)($X^{14}$) WEARSLTTGETGYIPSNYVAPVDSIQ (SEQ ID NO: 1), wherein ($X^1$) is R, N, Q, E, K, H, S, T, C, or D; ($X^2$) is E, T, D, Q, L, P, A, S, C, M, N, E, G, A, V or I; ($X^3$) is R, T, H, N, K, S, C, N or Q; ($X^4$) is S, W, T, C, N, Q, F or Y; ($X^5$) is T, H, L, F, C, S, M, N, Q, R, K, G, A, V, I, P, Y or W; ($X^6$) is D, Q, H, E, S, T, C, N, R or K; ($X^7$) is D, N, R, E, Q, S, T, C, K or D; ($X^8$) is M, W, G, F, A, T, C, S, N, Q, Y, V, L, I or P; ($X^9$) is T, H, S, D, C, N, Q, R, K, E or absent; ($X^{10}$) is V, T, Q, G, A, L, I, P, S, C, M, N or absent; ($X^{11}$) is P, A, D, G, K, V, L, I, E, R, M, H or absent; ($X^{12}$) is N, V, P, I, E, T, S, A, G, L, C, M, Q or D; ($X^{13}$) is D, E, T, P, G, A, V, L, I, S, C, M, N or Q, and ($X^{14}$) is W, Y, L, G, A, V, I, P, M, or F; (b) an amino acid sequence which is at least 85% identical to the amino acid sequence of (a), wherein the identity determination excludes amino acid positions ($X^1$) to ($X^{14}$).

In a preferred embodiment of the invention amino acid positions ($X^1$) to ($X^{14}$) are selected from ($X^1$) is R, N, Q, E or K; ($X^2$) is E, T, D, Q, L, P or A; ($X^3$) is R, T, H or N; ($X^4$) is S or W; ($X^5$) is T, H, L or F; ($X^6$) is D, Q or H; ($X^7$) is D, N, R, E, Q or S; ($X^8$) is M, W, G, F, A, S or T; ($X^9$) is T, H, S, D or absent; ($X^{10}$) is V, T, Q or absent; ($X^{11}$) is P, A, D, G, K or absent; ($X^{12}$) is N, V, P, I, E, T or S; ($X^{13}$) is D, E, T or P, and ($X^{14}$) is W, Y or L.

DETAILED DESCRIPTION OF THE PREFERRED EMBODIMENTS

The term "polypeptide" as used herein describes linear molecular chains of amino acids, including single chain proteins or their fragments, containing more than about 50 amino acids. Polypeptides may further form oligomers consisting of at least two identical or different molecules. The corresponding higher order structures of such multimers are, correspondingly, termed homo- or heterodimers, homo- or heterotrimers etc. Homodimers, trimers etc. also fall under the definition of the term "polypeptide". Furthermore, peptidomimetics of such polypeptides where amino acid(s) and/or peptide bond(s) have been replaced by functional analogs are also encompassed by the invention. Such functional analogues include all known amino acids other than the 20 gene-encoded amino acids, such as selenocysteine. The term "polypeptide" also refers to naturally modified polypeptides where the modification is effected e.g. by glycosylation, acetylation, phosphorylation and similar modifications which are well known in the art.

Also comprised by the present invention are fragments of the polypeptide of the invention which substantially retain binding to a chymase. In this regard it is preferred with increasing preference that the fragments comprise at least 30 amino acids, at least 35 amino acids, at least 40 amino acids, or at least 45 amino acids. It is moreover preferred that in the fragment the amino acid positions corresponding to the RT- and src-lop and the amino acids which are adjacent (1, 2, or 3 adjacent amino acid positions) to these loops as defined herein below are retained.

The term "binding to a chymase" requires that the polypeptides of the invention have a specific (in vivo and/or in vitro) binding affinity to a chymase, preferably a human chymase, and more preferably the chymase of SEQ ID NO: 16. Preferably, the polypeptides of the invention bind to chymase with a $K_D$ of $10^{-7}$ to $10^{-12}$ M, more preferably $10^{-8}$ to $10^{-12}$ M, most preferably $10^{-9}$ to $10^{-12}$ M.

SEQ ID NO: 17 is the amino acid sequence of the SH3 domain of the human Fyn kinase (aa 83-145 of Fyn kinase as reported by Kawakami et al. and Semba et al. in 1986). SEQ ID NO: 17 reads:

(SEQ ID NO: 17)
GVTLFVALYDY<u>EARTEDD</u>DLSFHKGEKFQIL<u>NSSE</u>GDWWEARSLTTGETG

YIPSNYVAPVDSIQ

In SEQ ID NO: 17 as shown above, the sequences of the RT-Src and the n-Src loop are underlined and double-underlined, respectively. Erpel et al. ("Mutational analysis of the Src SH3 domain: the same residues of the ligand binding surface are important for intra- and intermolecular interactions." Embo J. 14(5): 963-75, 1995) investigated the influence of mutations in the RT and n-Src loops of Src SH3 domains and demonstrated that mutations in both loops which are adjacent to the hydrophobic surface could influence the ability of this domain to participate in inter- and intramolecular associations. Moreover, EP 2054432 shows that mutations in and adjacent to the RT-Src and/or the n-Src loop determine the binding specificity of an SH3 domain. It is preferred with regard to the present invention that the sequence calculation according to item (b) above, further excludes the amino acid position A between ($X^1$) and ($X^2$) and the amino acid position G between ($X^{12}$) and ($X^{13}$), because these amino acids positions are within the RT-Src and the n-Src loop or adjacent to these loops.

The amino acid sequence of Fyn SH3 is fully conserved among man, mouse, rat and monkey (gibbon). Chicken Fyn SH3 differs in one, the one of *Xenopus laevis* in two amino acid positions from the corresponding human domain. Just as other SH3 domains the Fyn SH3 is composed of two antiparallel β-sheets and contains two flexible loops (called RT-Src and n-Src-loops) in order to interact with other proteins.

SEQ ID NO: 1 as recited herein above is derived from the amino acid sequence of the SH3 domain of the human Fyn kinase (SEQ ID NO: 17). In more detail, SEQ ID NO: 1 is a consensus sequence resulting from an alignment of SEQ ID NOs: 2 to 15 (cf. FIG. 1). As it is evident from FIG. 1, positions ($X^1$) to ($X^{14}$) are either in or adjacent to the RT- and src-loop of the Fyn Kinase SH3 domain of SEQ ID NO: 17. These amino acids positions determine the binding specificity to the chymase.

In accordance with the present invention, the term "percent (%) sequence identity" describes the number of matches ("hits") of identical nucleotides/amino acids of two or more aligned nucleic acid or amino acid sequences as compared to the number of nucleotides or amino acid residues making up the overall length of the template nucleic acid or amino acid sequences. In other terms, using an alignment, for two or more sequences or subsequences the percentage of amino acid residues or nucleotides that are the same (e.g. 85%, 90% or 95% identity) may be determined, when the (sub)sequences are compared and aligned for maximum correspondence over a window of comparison, or over a designated region as measured using a sequence comparison algorithm as known in the art, or when manually aligned and visually inspected. The sequences which are compared to determine sequence identity may thus differ by substitution(s), addition(s) or deletion(s) of nucleotides or amino acids. This definition also applies to the complement of a test sequence.

The skilled person is also aware of suitable programs to align nucleic acid sequences. The percentage sequence identity of polypeptide sequences can, for example, be determined with programmes as the above explained programmes CLUSTLAW, FASTA and BLAST. Preferably the BLAST programme is used, namely the NCBI BLAST algorithm (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402).

With regard to the sequence identity as recited in item (b) herein above, it is preferred with increasing preference that the sequence identity is at least 90%, at least 95%, or at least 98%.

The phrase "the identity determination excludes amino acid positions ($X^1$) to ($X^{14}$)" as used herein specifies that the calculation of the sequence identity with regard to SEQ ID NO. 1 does not take into a account amino acid positions ($X^1$) to ($X^{14}$) but is confined to the remainder of the 51 amino acids positions of SEQ ID NO: 1.

The term "chymase" refers to an enzyme, in more detail a serine protease of the Enzyme Commission number EC 3.4.21.39. As described herein above, chymase shows peptidolytic activity and is involved in a variety of organic functions and diseases. In more detail, chymase is a chymotrypsin-like enzyme that is expressed in the secretory granule of mast cells (Miller H. and Pemberton A., (2002), Immunity, 105, p. 375-390). Upon release, it has been described to degrade the extracellular matrix (e.g., proteoglycans, collagen, elastin, fibronectin), induce leukocyte migration and cytokine production, activate TGF-beta and MMP-9, and promote tissue remodeling (de Garavilla L. et al. (2005) J Biol Chem, 280(18) p. 18001-18007 and Takai S. et al. (2010) J Pharmacol Sci, 113(4), p. 301-309). In addition to these pro-inflammatory effects upon release from the granules of mast cells in different types of tissues, chymase has been found in mast cells in the human heart, where it cleaves angiotensin I to form angiotensin II (Urata et al. (1993) J Clin Invest, 91(4), p. 1269-1281). As it is evident from the sequence alignment of SEQ ID NOs 2 to 15 in FIG. 1, amino acid positions ($X^1$) to ($X^{14}$) are either within or adjacent to the RT- or src-loop of the SH3 domain of the Fyn Kinase. As discussed herein above, the amino acid positions in RT- and/or the src-loop determine the binding specificity to a target molecule. The examples herein below show that the amino acids listed for amino acid positions ($X^1$) to ($X^{14}$) confer binding specificity to a chymase, in particular to the chymase having SEQ ID NO: 16. In more detail, the sequence alignment of SEQ ID NOs 2 to 15 of the invention in FIG. 1 shows that amino acids positions ($X^1$) to ($X^{14}$) are selected from ($X^1$) is R, N, Q, E or K; ($X^2$) is E, T, D, Q, L, P or A; ($X^3$) is R, T, H or N; ($X^4$) is S or W; ($X^5$) is T, H, L or F; ($X^6$) is D, Q or H; ($X^7$) is D, N, R, E, Q or S; ($X^8$) is M, W, G, F, A, S or T; ($X^9$) is T, H, S, D or absent; ($X^{10}$) is V, T, Q or absent; ($X^{11}$) is P, A, D, G, K or absent; ($X^{12}$) is N, V, P, I, E, T or S; ($X^{13}$) is D, E, T or P, and ($X^{14}$) is W, Y or L. The other amino acids listed for amino acid positions ($X^1$) to ($X^{14}$) in the first embodiment of the invention as recited herein above specify conservative amino acid substitutions. As defined in more detail herein below, a conservative substitution specifies the replacement of an amino acid with another amino acid having a chemical property similar to the amino acid that is replaced. Therefore, it can be expected that all amino acids listed for amino acid positions ($X^1$) to ($X^{14}$) confer binding specificity to a chymase.

As it is further evident from the sequence alignment of SEQ ID NOs 2 to 15 in FIG. 1, not only amino acid positions ($X^1$) to ($X^{14}$) may differ between the amino acid sequence of SEQ ID NOs 2 to 15 but also additional amino acids positions which are not within or directly adjacent to the RT- and/or src-loop of SH3 domain of the Fyn kinase (SEQ ID NO: 17). These amino acids differences are not essential to the binding specificity of SEQ ID NOs. 2 to 15. Thus, it is evident that in the polypeptide of SEQ ID NO: 1 additional amino acid positions outside the RT- and/or src-loop of SH3 domain of the Fyn kinase and outside the amino acid positions adjacent thereto, in particular outside amino acid positions ($X^1$) to ($X^{14}$), may be exchanged or deleted, or further amino acids may be added, without substantially interfering with the binding specificity to chymase. If amino acids are exchanged, conservative exchanges are preferred.

A conservative substitution comprises the substitution of an amino acid with another amino acid having a chemical property similar to the amino acid that is substituted. Preferably, the conservative substitution is a substitution selected from the group consisting of: (i) a substitution of a basic amino acid with a different basic amino acid; (ii) a substitution of an acidic amino acid with a different acidic amino acid; (iii) a substitution of an aromatic amino acid with a different aromatic amino acid; (iv) a substitution of a non-polar, aliphatic amino acid with a different non-polar, aliphatic amino acid; and (v) a substitution of a polar, uncharged amino acid with a different polar, uncharged amino acid. A basic amino acid is selected from the group consisting of arginine, histidine, and lysine. An acidic amino acid is selected from aspartate or glutamate. An aromatic amino acid is selected from the group consisting of phenylalanine, tyrosine and tryptophane. A non-polar, aliphatic amino acid is selected from the group consisting of glycine, alanine, valine, leucine, methionine, isoleucine and proline. A polar, uncharged amino acid is selected from the group consisting of serine, threonine, cysteine, asparagine and glutamine. In contrast to a conservative amino acid substitution, a non-conservative amino acid substitution is the exchange of one amino acid with any amino acid that does not fall under the above-outlined conservative substitutions (i) through (v).

Thus, in a further preferred embodiment also encompassed by the invention are amino acid sequences which are with increasing preference at least 85%, at least 90%, at least 95%, or at least 98% identical to the amino acid sequence of SEQ ID NO: 1, wherein ($X^1$) to ($X^{14}$) are selected from the distinct amino acids shown above, or an amino acid sequence which is with increasing preference at least 85%, at least 90%, at least 95%, or at least 98% identical to the amino acid sequence of SEQ ID NO: 1, wherein ($X^1$) to ($X^{14}$) are selected from the distinct amino acids shown above, and wherein the identity determination excludes amino acid positions ($X^1$) to ($X^{14}$).

In a preferred embodiment the polypeptide of the invention comprises an amino acid sequence selected from the group consisting of any one of SEQ ID NOs 2 to 15.

As it is shown in the examples herein below, SEQ ID NOs 2 to 15 were found to bind to chymase, in more detail to the chymase having SEQ ID NO: 16. As it is well known, minor changes in an amino acid sequence such as deletion, addition or substitution of one, a few or even several amino acids may lead to a mutant form of the original protein which has substantially identical properties. Therefore, also encompassed by the present invention is a polypeptide comprising an amino acid sequence which is at least 85%, preferably at least 90%, more preferably at least 95% and most preferred at let 98% identical to any one of SEQ ID NOs 2 to 15.

According to a further preferred embodiment the polypeptide of the invention interferes with chymase activity.

The term "polypeptide interfering with chymase activity" as used herein defines that the polypeptide has the capability to reduce or completely abolish the enzymatic activity of a chymase, which is described herein above in detail. In this regard, it preferred with increasing preference that polypeptide inhibits the activity of the chymase by at least 10%, at least 20%, at least 30%, at least 40%, at least 50%, at least 60%, at least 70%, at least 80%, at least 90%, at least 95%, or 100%.

According to another preferred embodiment the chymase of the invention has the amino acids sequence of SEQ ID NO: 16.

As it is evident from the examples herein below, the human chymase having SEQ ID NO: 16 has been used as the target protein in order to identify the polypeptides having SEQ ID NOs 2 to 15.

The invention furthermore relates to a fusion protein comprising the polypeptide of the invention fused to the $F_c$ domain of an antibody, an albumin binder, an albumin, an IgG binder or an antibody.

The term "fusion protein" as used herein is in general terms directed to a polypeptide constructs generated through the joining of two or more genes which code for separate polypeptides. In other words, translation of this fusion gene results in a single polypeptide with functional properties derived from each of the original polypeptides. The polypeptides may either be directly fused or via a linker, i.e. a short peptide sequence. In general, fusion proteins are generated artificially by recombinant DNA technology well know to the skilled person. However, polypeptides and fusion proteins of the invention may be prepared by any of the many conventional and well known techniques such as plain organic synthetic strategies, solid phase-assisted synthesis techniques or by commercially available automated synthesizers. Fusion proteins may be used in biological research or therapeutics.

Also encompassed by the invention are fusion proteins comprising the polypeptide of the invention fused to a cytokine or chemokine. Such fusion proteins are described herein below in more detail in connection with the fusion construct of the invention. Also further detailed herein below and as known to the skilled person, fusion proteins comprising a cytokine or chemokine are particularly useful for medical purposes.

Preferably, the Fc domain is one or more human functional Fc domains which allow(s) for extending the in vivo half-life of the polypeptides of the invention and some of which direct a mammal's immune response to a site of specific target binding of the inventive polypeptide component of the fusion protein, e.g. in therapeutic, prophylactic and/or diagnostic applications as described herein below. The polypeptides of the invention can be fused either to the N- or C-terminus of one or more functional Fc domains or to both the N- and the C-terminus of one or more Fc domains. It is preferred that the fusion proteins of the invention comprise multimers, preferably tetramers, trimers or most preferably dimers of the polypeptides of the invention fused to at least one side, preferably to the N-terminus of one or more, preferably one Fc domain.

A "functional Fc domain" of an antibody is a term well known to the skilled artisan and defined on the basis of papain cleavage of antibodies. Depending on the amino acid sequence of the constant region of their heavy chains, immunoglobulins are divided in the classes: IgA, IgD, IgE, IgG and IgM, and several of these may be further divided into subclasses (isotypes), e.g. IgGI, IgG2, IgG3, and IgG4, IgA1, and IgA2. According to the heavy chain constant regions the different classes of immunoglobulins are called [alpha], [delta], [epsilon], [gamma], and [mu], respectively. The functional Fc domain of an antibody is directly involved in ADCC (antibody-dependent cell-mediated cytotoxicity) and CDC (complement-dependent cytotoxicity) based on complement activation, C1q binding and Fc receptor binding. The four human IgG isotypes bind different receptors, such as the neonatal Fc receptor, the activating Fc gamma receptors, FcγRI, FcγRIIa, and FcγRIIIa, the inhibitory receptor FcγRIIb, and C1q with different affinities, yielding very different activities. It is known that the affinities to activating and inhibiting receptors of an Fc domain of a human antibody can be engineered and modified (see Strohl W. (2009) Curr Opin Biotechnol, 20, p. 685-691). As mentioned above, the invention therefore comprises Fc fusion(s) which contains a functional Fc domain from preferably human origin, preferably a human functional Fc domain of an IgG1 antibody which allow(s) for extending the in vivo half-life of the polypeptides of the invention.

In a more preferred embodiment of the present invention, the Fc domain is one or more engineered human functional Fc domains of an IgGI with activating or silenced effector functions, preferably one or more engineered human functional Fc domains of an IgG1 with silenced effector functions, and even more preferably one or more engineered human functional Fc domains of an IgG1 with silenced effector functions with a mutation in L234 and L235, numbering according to EU index of Kabat (see Johnson G. and Wu T. T. (2000) Nucleic Acids Res. 28, p. 214-218), and most preferred with the mutation L234A and L235A.

Examples of an albumin binder, and an IgG binder are described in Gebauer and Skerra (2009), 13:245-255. Accordingly, preferred Examples of albumin binders and an IgG binders are human single Ig domains (dubbled Albumin Dab), nanobodies, naturally occurring albumin binding domain (ABD) derived from streptococcal protein G, and domain that binds to IgG.

Such fusion proteins, for example, increase the half life of the polypeptide of the invention upon administration to a patient, in particular in the blood circulation system.

The invention furthermore relates to a nucleic acid molecule encoding the polypeptide of the invention or the fusion protein of the invention.

The term "nucleic acid molecule", in accordance with the present invention, includes DNA, RNA and PNA. It is understood that the term "RNA" as used herein comprises all forms of RNA including mRNA. The term "nucleic acid molecule" is interchangeably used in accordance with the invention with the term "polynucleotide".

The nucleic acid molecule of the invention may also comprise regulatory regions or other untranslated regions. Said nucleic acid molecule may comprise heterologous nucleic acid which may encode heterologous proteinaceous material thus giving rise, e.g., to fusion proteins as described herein above.

Encompassed by the present invention are nucleic acid molecules that encode polypeptides having at least 85% identity (more preferred at least 90%, even more preferred at least 95% and most preferred at least 98% identity) at the amino acid level with the polypeptide depicted by any one of SEQ ID NO: 1 and in accordance with item (b) as defined herein above in the first embodiment of the invention.

The invention also relates to a vector comprising the nucleic acid molecule of the invention.

Preferably, the vector is a plasmid, cosmid, virus, bacteriophage or another vector used e.g. conventionally in genetic engineering.

The nucleic acid molecule of the invention may be inserted into several commercially available vectors. Non-limiting examples include prokaryotic plasmid vectors, such as the pUC-series, pBluescript (Stratagene), the pET-series of expression vectors (Novagen) or pCRTOPO (Invitrogen) and vectors compatible with an expression in mammalian cells like pREP (Invitrogen), pcDNA3 (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pCINeo (Promega). Plant expression vectors comprise pGEM-T (Promega), pCAMBIA 1391 (Cambia), GATEWAY (Invitrogen), pGreen and pGreenII (PGREEN). Examples for plasmid vectors suitable for *Pichia pastoris* comprise e.g. the plasmids pA0815, pPIC9K and pPIC3.5K (all Invitrogen).

The nucleic acid molecule referred to above may also be inserted into vectors such that a translational fusion with another polynucleotide is generated. The other polynucleotide may encode a protein which may e.g. increase the solubility, half-life and/or facilitate the purification of the fusion protein. The vectors may also contain an additional expressible polynucleotide coding for one or more chaperones to facilitate correct protein folding. For vector modification techniques, see Sambrook and Russel (2001), loc. cit. Generally, vectors can contain one or more origin of replication (ori) and inheritance systems for cloning or expression, one or more markers for selection in the host, e. g., antibiotic resistance, and one or more expression cassettes. Suitable origins of replication (oil) include, for example, the Col E1, the SV40 viral and the M 13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of transcription (e. g., translation initiation codon, promoters, such as naturally-associated or heterologous promoters and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers. Preferably, the polynucleotide of the invention is operatively linked to such expression control sequences allowing expression in prokaryotes or eukaryotic cells. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the polynucleotide of the invention. Such leader sequences are well known in the art.

Furthermore, it is preferred that the vector comprises a selectable marker. Examples of selectable markers include neomycin, ampicillin, and hygromycine, kanamycin resistance and the like. Specifically-designed vectors allow the shuttling of DNA between different hosts, such as bacteria-fungal cells or bacteria-animal cells (e. g. the Gateway® system available from Invitrogen).

An expression vector according to this invention is capable of directing the replication, and the expression, of the polynucleotide and encoded enzyme of this invention. Suitable expression vectors which comprise the described regulatory elements are known in the art.

The nucleic acid molecules as described herein above may be designed for direct introduction or for introduction via liposomes, phage vectors or viral vectors (e.g. adenoviral, retroviral) into a cell. Additionally, baculoviral systems or systems based on Vaccinia Virus or Semliki Forest Virus can be used as eukaryotic expression systems for the nucleic acid molecules of the invention.

A typical mammalian expression vector contains the promoter element, which mediates the initiation of transcription of mRNA, the protein coding sequence, and signals required for the termination of transcription and polyadenylation of the transcript. Moreover, elements such as origin of replication, drug resistance gene, regulators (as part of an inducible promoter) may also be included. The lac promoter is a typical inducible promoter, useful for prokaryotic cells, which can be induced using the lactose analogue isopropylthiol-b-D-galactoside. ("IPTG"). For recombinant expression and secretion, the polynucleotide of interest may be ligated between e.g. the PelB leader signal, which directs the recombinant protein in the periplasm and the gene III in a phagemid called pHEN4 (described in Ghahroudi et al, 1997, FEBS Letters 414:521-526). Additional elements might include enhancers, Kozak sequences and intervening sequences flanked by donor and acceptor sites for RNA splicing. Highly efficient transcription can be achieved with the early and late promoters from SV40, the long terminal repeats (LTRs) from retroviruses, e.g., RSV, HTLVI, HIVI, and the early promoter of the cytomegalovirus (CMV). However, cellular elements can also be used (e.g., the human actin promoter). Alternatively, the recombinant polypeptide can be expressed in stable cell lines that contain the gene construct integrated into a chromosome. The co-transfection with a selectable marker such as dhfr, gpt, neomycin, hygromycin allows the identification and isolation of the transfected cells. The transfected nucleic acid can also be amplified to express large amounts of the encoded polypeptide. As indicated above, the expression vectors will preferably include at least one selectable marker. Such markers include dihydrofolate reductase, G418 or neomycin resistance for eukaryotic cell culture and tetracycline, kanamycin or ampicillin resistance genes for culturing in $E.\ coli$ and other bacteria.

In a further embodiment the invention relates to a host cell comprising the nucleic acid molecule of the invention or the vector of the invention.

In a preferred embodiment the host cell is an isolated cell which may be part of a cell culture.

Suitable prokaryotic host cells comprise e.g. bacteria of the species $Escherichia$, $Bacillus$, $Streptomyces$ and $Salmonella$ $typhimurium$. Suitable eukaryotic host cells are e.g. fungal cells, inter alia, yeasts such as $Saccharomyces\ cerevisiae$ or $Pichia\ pastoris$ or insect cells such as $Drosophila$ S2 and $Spodoptera$ Sf9 cells and plant cells as well as mammalian cells.

Mammalian host cells that could be used include, human Hela, HEK293, H9 and Jurkat cells, mouse NIH3T3 and C127 cells, Cos 1, Cos 7 and CV1, quail QC1-3 cells, mouse L cells and Chinese hamster ovary (CHO) cells.

In a more preferred embodiment, said cell is a primary cell or primary cell line. Primary cells are cells which are directly obtained from an organism. Suitable primary cells are, for example, mouse embryonic fibroblasts, mouse primary hepatocytes, cardiomyocytes and neuronal cells as well as mouse muscle stem cells (satellite cells) and stable, immortalized cell lines derived thereof. Also within the scope of the present invention are primary mammalian cells such as mouse embryonic fibroblasts (MEF). Alternatively, the recombinant (poly)peptide can be expressed in stable cell lines that contain the gene construct integrated into a chromosome.

Appropriate culture media and conditions for the above-described host cells are well-known in the art.

The invention also relates to a fusion construct comprising the polypeptide of the invention fused to a pharmaceutically active compound, a diagnostically active compound and/or a component modulating serum half-life.

A "fusion construct" has used herein defines the fusion of the polypeptide of the invention to a compound. The compound may be selected from the group consisting of a pharmaceutically active compound, a diagnostically active compound and/or a component modulating serum half-life. The compound may either be a proteinous compound or a non-proteinous compound. In the case the compound is a proteinous compound (e.g. a cytokine or chemokine as described herein below), the fusion construct is also a fusion protein as defined herein above, in other words, the term "fusion constructs" comprises fusion proteins. The compound may either be directly fused to the polypeptide or via a linker. The linker according to the invention is preferably selected from the group consisting of alkyl with 1 to 30 carbon atoms, polyethylene glycol with 1 to 20 ethylene moieties, polyalanine with 1 to 20 residues, caproic acid, substituted or unsubstituted poly-p-phenylene and triazol.

In a further preferred embodiment, said linker is selected from the group consisting of amino-n-alkyl, mercapto-n-alkyl, amino-n-alkyl-X-alkyl, mercapto-n-alkyl-X-alkyl, wherein X is selected from the group consisting of O, S—S and $SO_2$ and wherein the alkyl groups independently from each other have from 1 to 30 carbon atoms, preferably 3, 6 or 12 carbon atoms; or oligoethylenglycols having from one to about ten ethylenglycol moieties, preferably tri- or hexa-ethylenglycol. These and further suitable linkers are well known in the art and commercially available (see, for example, the catalogue from Glen Research, 22825 Davis Drive, Sterling, Va., 20164 USA). Further examples of linkers are the following: 5'-amino-modifiers (see e.g. B. A. Connolly and P. Rider, Nucleic Acids Res., 1985, 13, 4485; B. S. Sproat, B. S. Beijer, P. Rider, and P. Neuner, Nucleic Acids Res., 1987, 15, 4837; R. Zuckerman, D. Corey, and P. Shultz, Nucleic Acids Res., 1987, 15, 5305; P. Li, et al., Nucleic Acids Res., 1987, 15, 5275; G. B. Dreyer and P. B. Dervan, Proc. Natl. Acad. Sci. USA, 1985, 82, 968.); 5'-thiol-modifier C6 (see e.g. B. A. Connolly and P. Rider, Nucleic Acids Res., 1985, 13, 4485; B. S. Sproat, B. S. Beijer, P. Rider, and P. Neuner, Nucleic Acids Res., 1987, 15, 4837; R. Zuckerman, D. Corey, and P. Shultz, Nucleic Acids Res., 1987, 15, 5305; P. Li, et al., Nucleic Acids Res., 1987, 15, 5275.); 5'-thiol-modifier C6 S—S and thiol group at the 3'-terminus (see e.g. B. A. Connolly and R. Rider, Nucleic Acids Res., 1985, 13, 4485; B. A. Connolly, Nucleic Acids Res., 1987, 15, 3131-3139; N. D. Sinha and R. M. Cook, Nucleic Acids Res., 1988, 16, 2659; A. Kumar, S. Advani, H. Dawar, and G. P. Talwar, Nucleic Acids Res., 1991, 19, 4561; R. Zuckermann, D. Corey, and P. Schultz, Nucleic Acids Res., 1987, 15, 5305; K. C. Gupta, P. Sharma, S. Sathyanarayana, and P. Kumar, Tetrahedron Lett., 1990, 31, 2471-2474; U. Asseline. E. Bonfils, R. Kurfurst, M. Chassignol, V. Roig, and N. T. Thuong, Tetrahedron, 1992, 48, 1233-1254; Gregg Morin, Geron Corporation, Personal Communication.); spacer C3, spacer C12, and dspacer phosphoramidites (see e.g. M. Durard, K. Chevrie, M. Chassignol, N. T. Thuong, and J. C. Maurizot, Nucleic Acids Res., 1990, 18, 6353; M. Salunkhe, T. F. Wu, and R. L. Letsinger, J. Amer. Chem. Soc, 1992, 114, 8768-8772; N. G. Dolinnaya, M. Blumenfeld, I. N. Merenkova, T. S. Oretskaya, N. F. Krynetskaya, M. G. Ivanovskaya, M. Vasseur, and Z. A. Shabarova, Nucleic Acids Res., 1993, 21, 5403-5407; M. Takeshita, C. N. Chang, F. Johnson, S. Will, and A. P. Grollman, J. Biol. Chem., 1987, 262, 10171-10179; M. W. Kalnik, C. N. Chang, A. P. Grollman, and D. J. Patel, Biochemistry, 1988, 27, 924-931.); 3'-amino-modifier C7 CPG (see e.g. J. G. Zendegui, K. M. Vasquez, J. H. Tinsley, D. J. Kessler, and M. E. Hogan, Nucleic Acids Res., 1992, 20, 307.); 3'-Amino Photolabile C6 CPG (see e.g. D. J. Yoo and M. M. Greenberg, J. Org. Chem., 1995, 60, 3358-3364.; H. Venkatesan and M. M. Greenberg, J. Org. Chem., 1996, 61, 525-529; D. L. McMinn and M. M. Greenberg, Tetrahedron, 1996, 52, 3827-3840.

The component modulating serum half-life is preferably polyethylene glycol (PEG).

In an preferred embodiment of the invention the pharmaceutically active compound or diagnostically active compound is selected from the group consisting of
(a) a fluorescent dye,
(b) a photosentisizer,
(c) a radionuclide,
(d) a contrast agent for medical imaging,
(e) a cytokine
(f) a toxic compound
(g) a chemokine
(h) a pro-coagulant factor
(i) an enzyme for pro-drug activation, or
(j) an ACE inhibitor, a Renin inhibitor, an ADH inhibitor, an Aldosteron inhibitor, or an Angiotensin receptor blocker.

The fluorescent dye is preferably a component selected from Alexa Fluor or Cy dyes.

The photosensitizer is preferably phototoxic red fluorescent protein KillerRed or haematoporphyrin.

The radionuclide is preferably either selected from the group of gamma-emitting isotopes, more preferably $^{99}$mTc, $^{231}$I, $^{111}$In, and/or from the group of positron emitters, more preferably $^{18}$F, $^{64}$Cu, $^{68}$Ga, $^{86}$Y, $^{124}$I, and/or from the group of beta-emitter, more preferably $^{131}$I, $^{90}$Y, $^{177}$Lu, $^{67}$Cu, or from the group of alpha-emitter, preferably $^{213}$Bi, $^{211}$At.

A contrast agent as used herein is a substance used to enhance the contrast of structures or fluids within the body in medical imaging. Common contrast agents work based on X-ray attenuation and magnetic resonance signal enhancement.

The cytokine is preferably selected from the group consisting of IL-2, IL-12, TNF-alpha, IFN alpha, IFN beta, IFN gamma, IL-10, IL-15, IL-24, GM-CSF, IL-3, IL-4, IL-5, IL-6, IL-7, IL-9, IL-11, IL-13, LIF, CD80, B70, TNF beta, LT-beta, CD-40 ligand, Fas-ligand, TGF-beta, IL-1alpha and IL-1 beta. As it is well-known in the art, cytokines may favour a pro-inflammatory or an anti-inflammatory response of the immune system. Thus, depending on the disease to be treated either fusion constructs with a pro-inflammatory or an anti-inflammatory cytokine may be favored. For example, for the treatment of inflammatory diseases in general fusion constructs comprising anti-inflammatory cytokines are preferred, whereas for the treatment of cancer in general fusion constructs comprising pro-inflammatory cytokines are preferred.

The toxic compound is preferably a small organic compound or a polypeptide, more preferably a toxic compound selected from the group consisting of calicheamicin, maytansinoid, neocarzinostatin, esperamicin, dynemicin, kedarcidin, maduropeptin, doxorubicin, daunorubicin, auristatin, Ricin-A chain, modeccin, truncated *Pseudomonas* exotoxin A, diphtheria toxin and recombinant gelonin.

The chemokine is preferably selected from the group consisting of IL-8, GRO alpha, GRO beta, GRO gamma, ENA-78, LDGF-PBP, GCP-2, PF4, Mig, IP-10, SDF-1 alpha/beta, BUNZO/STRC33, I-TAC, BLC/BCA-1, MIP-1 alpha, MIP-1 beta, MDC, TECK, TARC, RANTES, HCC-1, HCC-4, DC-CK1, MIP-3 alpha, MIP-3 beta, MCP-1-5, eotaxin, Eotaxin-2, I-309, MPIF-1, 6Ckine, CTACK, MEC, lymphotactin and fractalkine.

The pro-coagulant factor is preferably a tissue factor.

The enzyme for pro-drug activation is preferably an enzyme selected from the group consisting of carboxy-peptidases, glucuronidases and glucosidases.

The invention moreover relates to a pharmaceutical or diagnostic composition comprising the polypeptide of the invention, the fusion protein of the invention, the nucleic acid molecule of the invention, the vector of the invention, the host cell of the invention or the fusion construct of the invention.

As mentioned herein above, chymase is involves in many diseases. Accordingly the polypeptide of the invention, the fusion protein of the invention, the nucleic acid molecule of the invention, or the fusion construct of the invention is useful in targeting the nucleic acid molecule as described or interfering with the function of the polypeptide as described.

The pharmaceutical composition is preferably administered to mammals such as domestic and pet animals (see also below). Most preferred it is administered to humans. The pharmaceutical compositions described herein will be administered to the subject at a suitable dose.

The pharmaceutical composition for use in accordance with the present invention can be formulated in conventional manner according to methods found in the art, using one or more physiological carriers or excipient, see, for example Ansel et al., "Pharmaceutical Dosage Forms and Drug Delivery Systems", 7th edition, Lippincott Williams & Wilkins Publishers, 1999. The pharmaceutical composition may, accordingly, be administered orally, parenterally, such as subcutaneously, intravenously, intramuscularly, intraperitoneally, intrathecally, transdermally, transmucosally, subdurally, locally or topically via iontopheresis, sublingually, by inhalation spray, aerosol or rectally and the like in dosage unit formulations optionally comprising conventional pharmaceutically acceptable excipients.

The pharmaceutical composition of the invention may be administered as the sole active ingredient or in conjunction with, e.g. as an adjuvant to or in combination with, other drugs, e.g. immunosuppressive or immune modulating agents or other anti-inflammatory agents, e.g. for the treatment or prevention of diseases mentioned above. For example, the binding polypeptides and fusion proteins of the invention may be used in combination with immunosuppressive monoclonal antibodies, e.g. monoclonal antibodies with affinity to leukocyte receptors, e.g. MHC, CD2, CD3, CD4, CD7, CD8, CD25, CD28, CD40, CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (e.g. designated ATCC 68629) or a mutant thereof, e.g. LEA29Y; adhesion molecule inhibitors, e.g. LFA-I antagonists, ICAM-I or -3 antagonists, VCAM-4 antagonists or VLA-4 antagonists. In addition, the polypeptides and fusion proteins of the invention may be used in combination with DMARD (disease-modifying anti-rheumatic drugs), gold salts, sulphasalazine, anti-malarias, methotrexate, D-penicillamine, azathioprine, mycophenolic acid, cyclosporine A, tacrolimus, sirolimus, minocycline, leflunomide, glucocorticoids; a calcineurin inhibitor, e.g. cyclosporin A or FK 506; a modulator of lymphocyte recirculation, e.g. FTY720 and FTY720 analogs; a mTOR inhibitor, e.g. rapamycin, 40-O-(2-hydroxyethyl)-rapamycin, CCI779, ABT578, AP23573 or TAFA-93; an ascomycin having immuno-suppressive properties, e.g. ABT-281, ASM981, etc.; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; or a chemotherapeutic agent, e.g. paclitaxel, gemcitabine, cisplatinum, doxorubicin or 5-fluorouracil; anti-TNF agents, e.g. monoclonal antibodies to TNF, e.g. infliximab, adalimumab, CDP870, or receptor constructs to TNF-RI or TNF-RII, e.g. Etanercept, PEG-TNF-RI; blockers of proinflammatory cytokines, IL-1 blockers, e.g. Anakinra or IL-1 trap, AAL160, ACZ 885, IL-6 blockers; inhibitors or activators of proteases, e.g. metalloproteases, anti-IL-15 antibodies, anti-IL-6 antibodies, anti-IL-23 antibodies, anti-IL-22 antibodies, anti-IL-21 antibodies, anti-IL-12 antibodies, anti-IFN-gamma antibodies, anti-IFN-alpha antibodies, anti-CD20 antibodies, anti IL-17 antibodies, anti-IgGE antibodies, NSAIDs, such as aspirin or an anti-infectious agent. Other drugs may include an ACE inhibitor, a Renin inhibitor, an ADH inhibitor, an Aldosteron inhibitor, and an Angiotensin receptor blocker. Naturally, this list of agents for co-administration is not limiting nor complete.

In general terms the pharmaceutical composition of the invention is used in the treatment or prevention of a chymase-mediated disease or a chymase-mediated organ damage.

The diagnostic composition of the invention is useful in the detection of an undesired physiological chymase level, in particular the chymase of SEQ ID NO: 16, e.g. in different cells, tissues or another suitable sample, comprising contacting a sample with the polypeptide of the invention, the fusion protein of the invention, the nucleic acid molecule of the invention, or the fusion construct of the invention, and detecting the presence of a chymase, in particular the chymase of SEQ ID NO: 16 in the sample. Accordingly, the diagnostic composition of the invention may be used for assessing the onset or the disease status. As defined herein below, in particular organ damage, an inflammatory condition, a cardiovascular disease or cancer can be targeted with the polypeptide of the invention, the fusion protein of the invention, the nucleic acid molecule of the invention, or the fusion construct of the invention. In one aspect of the present invention described herein above, the polypeptide of the invention is linked to are fluorescent dye, a photosentisizer, a radionuclide, or a contrast agent for medical imaging. Such fusion constructs are particularly suitable for diagnostic applications.

The diagnostic composition of the invention can be administered as sole active agent or can be administered in combination with other agents, if the diagnostic composition is, for example, used to identify sites of undesired physiological chymase levels within a subject. In general terms the diagnostic composition of the invention is used in the diagnosis of a chymase-mediated disease or a chymase-mediated organ damage.

The dosage of the diagnostic and pharmaceutical compositions of the invention, will, of course, vary depending upon the particular polypeptide of the invention, the fusion protein of the invention, the nucleic acid molecule of the invention, the vector of the invention, the host cell of the invention, or the fusion construct of the invention, the individual patient group or patient, the optional presence of further medically active compounds and the nature and severity of the condition being treated. However, it is presently preferred that the diagnostic or pharmaceutical composition is used in dosages of about 0.01 mg to about 20 mg per kilogram body weight, preferably about 0.1 mg to about 5 mg per kilogram body weight. Preferably, the frequency of administration of the diagnostic or pharmaceutical composition is in the range of daily up to about once every 3 months, preferably about once every 2 weeks up to about once every 10 weeks, more preferably once every 4 to 8 weeks. A preferred dosage regimen involves the administration of the diagnostic or pharmaceutical compositions of the invention once per month to once every 2 to 3 months or less frequently.

According to one embodiment the pharmaceutical composition of the invention is for use in the treatment of organ damage, an inflammatory condition, a cardiovascular disease or cancer.

As it has been detailed herein above, chymase is known for its role in organ damage, inflammatory condition, cardiovascular disease and cancer.

In accordance with a preferred embodiment the inflammatory condition, cardiovascular disease or cancer is selected from the group consisting of allergy, asthma, chronic obstructive pulmonary disease, rheumatoid arthritis, ulcerative colitis, diabetes, Crohn's disease, cardiomyopathy, myocardial infarction, left ventricular hypertrophy, trachycardia-induced heart failure, unstable angina pectoris, restenosis, atherosclerosis, dermatitis, vascular proliferation after balloon catheter injury, and uterine cervical carcinoma.

In accordance with another preferred embodiment the organ damage of is induced by aortic aneurysm, diabetic retinopathy, fibrosis, ulcerative colitis or another inflammatory disease.

In a further embodiment the invention relates to a method for the identification of a polypeptide binding to a chymase (EC 3.4.21.39) comprising the steps of: (a) constructing a library of mutants derived from the FYN kinase SH3 domain having the amino sequence of SEQ ID NO: 17, (b) contacting the library of mutants constructed in (a) with a chymase (EC 3.4.21.39), and (c) isolating the mutants which bind to the chymase.

A "mutant" as used herein defines a polypeptide having at least one mutation as compared to the polypeptide of SEQ ID NO: 17. A mutation specifies any change of the amino acid sequence including the addition, deletion and substitution of amino acids. The mutations may also introduced in the nucleic acid molecules encoding the mutants. Methods for the generation of mutants are well-known in the art, and include, for example, random-mutagenesis techniques as well as site-directed mutagenesis techniques.

It is within the knowledge of the skilled person to perform this method. Detailed experimental guidance is, for example, known from Grabulovski et al. (2007), JBC, 282, p. 3196-3204 and EP 2054432. In this regard, it is preferred that chymase is biotinylated chymase and/or steps (b) and (c) involve an ELISA assay.

According to a preferred embodiment of the method the invention, in step (a) the library of mutants is generated by simultaneous randomization of at least one amino acid in or positioned up to two amino acids adjacent to the src loop and random substitution, deletion or addition of at least one amino acid in or positioned up to two amino acids adjacent to the RT loop of the FYN kinase SH3 domain having the amino sequence of SEQ ID NO: 17.

In accordance with another preferred embodiment of the method the invention the library comprises at least $1 \times 10^7$ mutants.

In this regard, it is more preferred that the library comprises at least $1 \times 10^8$ mutants and even more preferred that the library comprises at least $1 \times 10^9$ mutants.

The Figures show:

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 1—Sequence alignment of SEQ ID NOs 2 to 15.

FIG. 3—shows the monomeric size exclusions profiles of the following Fyn SH3-derived polypeptides of the invention: (A) Fyn SH3-derived polypeptide of the invention F12 (SEQ ID NO: 5), (B) Fyn SH3-derived polypeptide of the invention G2.3 (SEQ ID NO: 6), (C) Fyn SH3-derived polypeptide of the invention E3 (SEQ ID NO: 9), (D) Fyn SH3-derived polypeptide of the invention B5 (SEQ ID NO: 3), (E) Fyn SH3-derived polypeptide of the invention D7 (SEQ ID NO: 7), (F) Fyn SH3-derived polypeptide of the invention E4 (SEQ ID NO: 2), (G) Fyn SH3-derived polypeptide of the invention H2 (SEQ ID NO: 8), (H) Fyn SH3-derived polypeptide of the invention A4 (SEQ ID NO: 4)

EXAMPLES

Example 1

Figure 2:
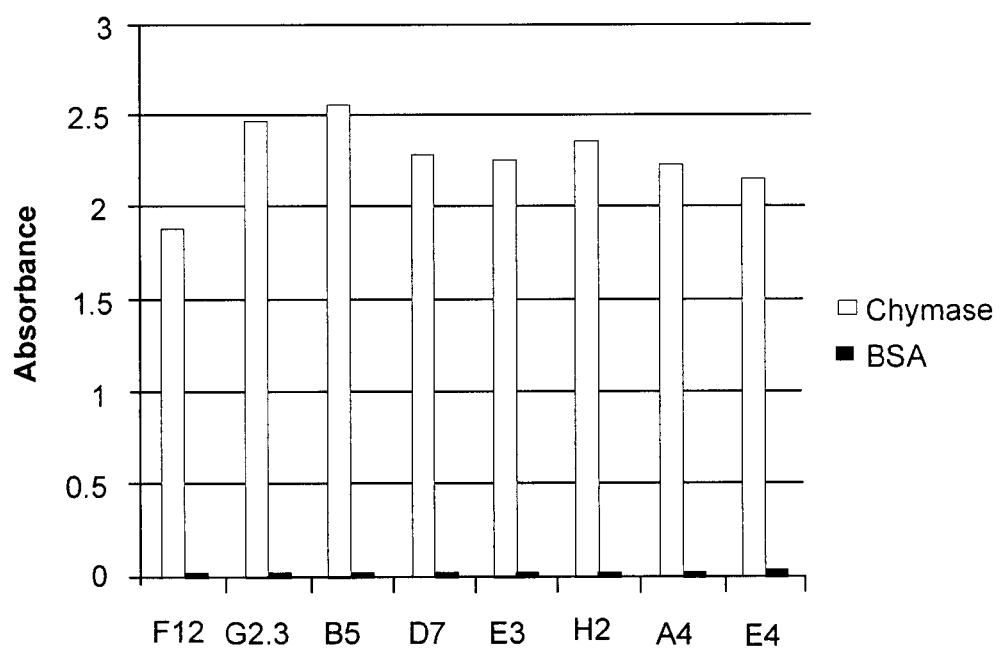
FIG. 2—shows the ELISA signals for binding of the indicated Fyn SH3-derived polypeptides of the invention to chymase. F12 is SEQ ID NO: 5, G2.3 is SEQ ID NO: 6, B5 is SEQ ID NO: 3, D7 is SEQ ID NO: 7, E3 is SEQ ID NO: 9, H2 is SEQ ID NO: 8, A4 is SEQ ID NO: 4, and E4 is SEQ ID NO: 2. See Table II. No ELISA signals could be detected for the binding to the irrelevant protein bovine serum albumin (BSA).
Figure 4:
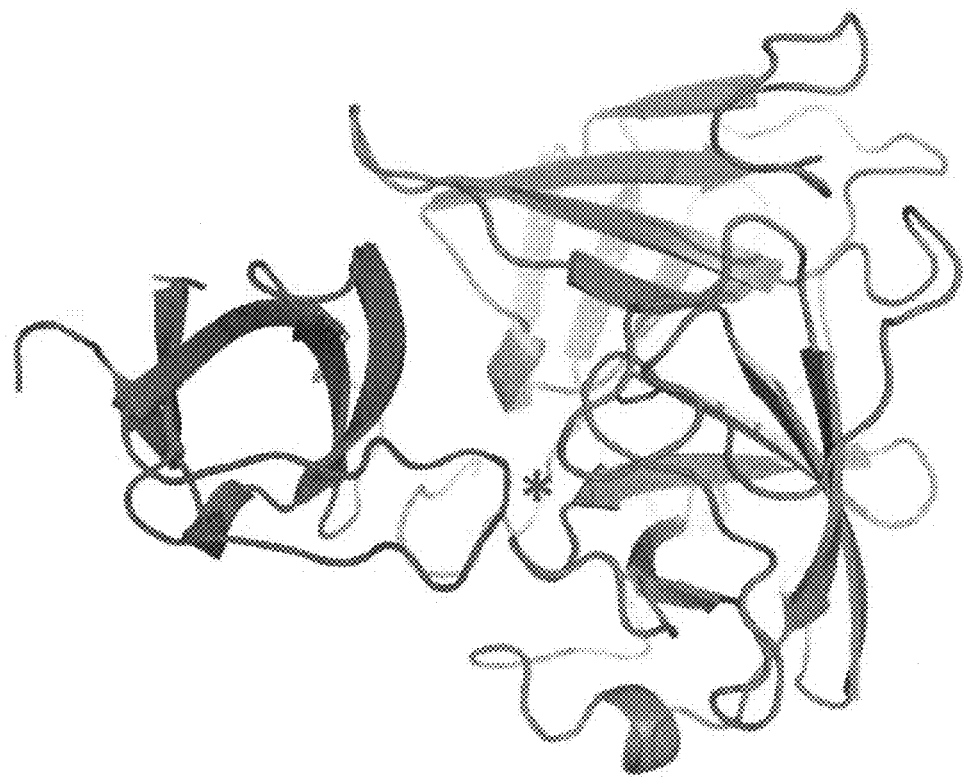
FIG. 4—shows the Complex of Fyn SH3-derived polypeptide of the invention A4 (SEQ ID NO: 4) (magenta) with chymase (green). The Fyn SH3-derived polypeptide of the invention A4 (SEQ ID NO: 4) blocks the active site (indicated with the *).
Figure 5:
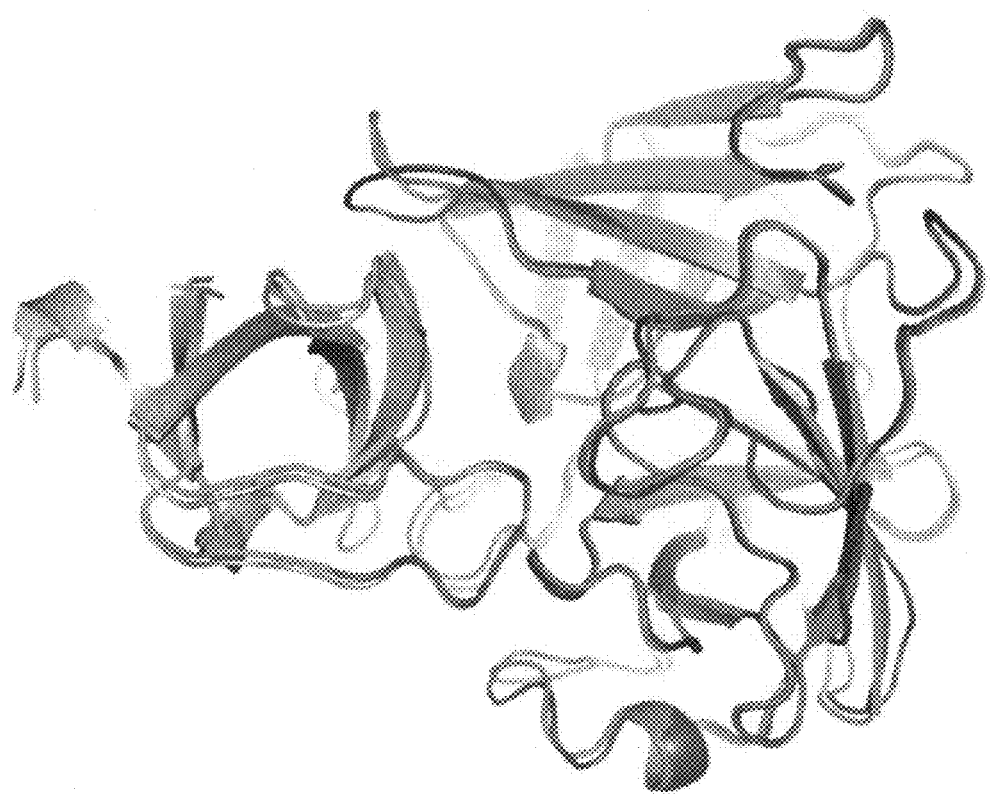
FIG. 5—shows the complex A4-chymase (green/cyan) and the E4-chymase (SEQ ID NO: 2) complex in plum/grey). The chymase-E4 complex shows exactly the same binding mode as the chymase-A4 (SEQ ID NO: 4) complex.
Figure 6:
FIG. 6—shows the complex chymase A4 (SEQ ID NO: 4) in green/cyan and the complex chymase-B5 (SEQ ID NO: 3) in yellow/salmon. The chymase-B5 complex shows exactly the same binding mode as the chymase-A4 complex.

Fyn SH3-Derived Polypeptides of the Invention Bind to Chymase as Determined by Monoclonal ELISA Using Bacterial Lysate Supernatants Containing the Fyn SH3-Derived Polypeptides of the Invention Methods:

DNA encoding the amino acid sequences shown in SEQ ID NOs: 2 to 15 were cloned into the cytosolic expression vector pQE-12 with a C-terminal myc and hexa his tag. After bacterial electroporation, bacterial lysates containing the Fyn SH3-derived polypeptides were produced as described in Bertschinger et al. (Bertschinger et al. (2007) Protein Eng Des Sel, 20(2), p. 57-68). Chymase was produced as described in Perspicace et al. (Perspicace et al. (2009) J Biomol Screen, 14(4), p. 337-349). The protein was biotinylated according to the manufacturer's instructions using EZ-link sulfo-NHS—SS-biotin (Perbio) and finally contained 3 biotin molecules per chymase molecule. For the ELISA experiment, biotinylated chymase was added to streptavidin-coated wells (StreptaWells, High Bind, Roche) at a concentration of 100 nM and after blocking with PBS, 2% milk (Rapilait, Migros, Switzerland), 40 µl of the bacterial supernatant containing the corresponding Fyn SH3-derived polypeptide were added to the wells together with 10 µl of an anti-myc antibody (9E10, at a final concentration of 10 µg/ml in PBS, 2% Milk). After incubating for 1 h and washing, detection was made with anti-mouse IgG HRP antibody conjugate (Sigma). Peroxidase activity was detected by adding BM blue POD substrate (Roche) and the reaction was stopped by adding 1M H$_2$SO$_4$.

The DNA sequence of the binders was verified by DNA sequencing (BigDye Terminator v3.1 cycle sequencing kit, ABI PRISM 3130 Genetic Analyzer, Applied Biosystems).

Results:

The amino acid sequences of Fyn SH3-derived chymase binders is presented in SEQ ID NOs: 2 to 15 as appended in the sequence listing. SEQ ID NOs: 2 to 15 read:

(E4)
SEQ ID NO: 2
GVTLFVALYDYNATRWTDLSFHKGEKFQILEFGPGDWWEARSLTTGETG
YIPSNYVAPVDSIQ (B5)
SEQ ID NO: 3
GVTLFVALYDYNATRWTDLSFHKGEKFQILDGDSGDWWEARSLTTGETG
YIPSNYVAPVDSIQ (A4)
SEQ ID NO: 4
GVTLFVALYDYQADRWTDLSFHKGEKFQILDASPPGDWWEARSLTTGET
GYIPSNYVAPVDSIQ (F12)
SEQ ID NO: 5
GVTLFVALYDYRAERSTDLSFHKGEKFQILDMTVPNGDWWEARSLTTGE
TGYIPSNYVAPVDSIQ (G2.3)
SEQ ID NO: 6
GVTLFVALYDYNATRWTDLSFHKGEKFQILDWTTANGDWWEARSLTTGE
TGYIPSNYVAPVDSIQ (D7)
SEQ ID NO: 7
GVTLFVALYDYQADRWTDLSFHKGEKFQILSFHVGDWWEARSLTTGETG
YIPSNYVAPVDSIQ (H2)
SEQ ID NO: 8
GVTLFVALYDYQADRWTDLSFHKGEKFQILRFDIGDWWEARSLTTGETG
YIPSNYVAPVDSIQ (E3)
SEQ ID NO: 9
GVTLFVALYDYQADRWTDLSFHKGEKFQILNASGPGDWWEARSLTTGET
GYIPSNYVAPVDSIQ (D2)
SEQ ID NO: 10
GVTLFVALYDYEAQTWHDLSFHKGEKFQILNSSEGEYWEARSLTTGETG
LIPSNYVAPVDSIQ (H11)
SEQ ID NO: 11
GVTLFVALYDYKAQRWTDLSFHKGEKFQILQAHQKTGDWWEARSLTTGE
TGLIPSNYVAPVDSIQ (B10)
SEQ ID NO: 12
GVTLFVALYDYEALHWHQLSFHKGEKSQILNSSEGTYWEARSLTTGETG
WIPSNYVAPGDSIQ (E5)
SEQ ID NO: 13
GVTLFVALYDYKAQRWLDLSFHEGEKFQILSTDSGDWWEARSLTTGETG
YIPSNYVAPVDSIQ (C5)
SEQ ID NO: 14
GVTLFVALYDYEAPTWLHLSFHKGEKFQILNSSEGPWWEARSLTTGETG
FIPSNYVAPVDSIQ (A8)
SEQ ID NO: 15
GVTLFVALYDYEAANWFQLSFHKGEKFQILNSSEGPLWEARSLTTGETG
GIPSNYVAPVDSIQ

Example 2

Purified Fyn SH3-Derived Polypeptides of the Invention Bind Specifically to Chymase as Determined by ELISA Methods:

Fyn SH3-derived polypeptides (SEQ ID NO: 2-9) were expressed and purified as described in Grabulovski et al. (Grabulovski et al. (2007) JBC, 282, p. 3196-3204). Biotinylated chymase or biotinylated bovine serum albumin (BSA) as an irrelevant target protein (Sigma; biotinylation was performed according to the manufacturers instructions using EZ-link sulfo-NHS—SS-biotin (Perbio)) was added to streptavidin-coated wells (StreptaWells, High Bind, Roche) at a concentration of 100 nM and after blocking with PBS, 2% milk (Rapilait, Migros, Switzerland), 50 µl of the corresponding Fyn SH3-derived polypeptide at a final concentration of 200 nM were added to the wells together with 50 µl of an anti-myc antibody (9E10, at a final concentration of 5 µg/ml in PBS, 2% Milk). After incubating for 1 h and washing, detection was made with anti-mouse IgG HRP antibody conjugate (Sigma). Peroxidase activity was detected by adding BM blue POD substrate (Roche) and the reaction was stopped by adding 1M H$_2$SO$_4$.

Results:

FIG. 2 shows the ELISA signals on chymase and BSA coated wells, indicating specific binding to chymase.

Example 3

Fyn SH3-Derived Polypeptides of the Invention are Monomeric and do not Aggregate as Determined by Size Exclusion Chromatography Methods After purification of the Fyn SH3-derived polypeptides (SEQ ID NOs: 2-9) as described in Example 2, size exclusion chromatography (SEC) was performed on an AKTA FPLC system using a Superdex 75 Column (5/150) (GE Healthcare).

Results

Size exclusion chromatography (SEC) profiles demonstrated that all selected constructs eluted mainly as single, monomeric peaks (see FIG. 3).

Example 4

Fyn SH3-Derived Polypeptides of the Invention Bind with High Affinity to Chymase as Determined by Surface Plasmon Resonance Experiments Methods:

Affinity measurements of selected Fyn SH3-derived polypeptides (SEQ ID NO: 2-9) were performed using a BIAcore 3000 instrument (Biacore). For the interaction analysis between biotinylated chymase and monomeric Fyn SH3-derived polypeptides, a streptavidin SA chip (Biacore) was immobilized with 1331 RU biotinylated chymase. The running buffer was PBS, 0.005% Tween 20. The interactions were measured at a flow of 30 μl/min and injections of different concentrations of Fyn SH3-derived chymase-binding polypeptides. All kinetic data of the interaction (separate kon/koff) were evaluated using BIA evaluation 3.2RC1 software Results:

The binding properties were analyzed by real-time interaction analysis on a BIAcore chip revealing the following dissociation constants (KD) and $k_{off}$ values for the Fyn SH3-derived polypeptides (Table I):

TABLE I

Dissociation konstants and $k_{off}$ values of Fyn SH3-derived polypeptides.

| Clone | SEQ ID NO: | $K_D$ (nM) | $k_{off}$ (s$^{-1}$) |
|---|---|---|---|
| F12 | 5 | 36.0 | $2.3 \times 10^{-3}$ |
| G2.3 | 6 | 14.0 | $8.2 \times 10^{-3}$ |
| B5 | 3 | 5.0 | $3.6 \times 10^{-3}$ |
| D7 | 7 | 15.0 | $1.1 \times 10^{-2}$ |
| E3 | 9 | 13.0 | $9.3 \times 10^{-3}$ |
| H2 | 8 | 32.0 | $2.1 \times 10^{-3}$ |
| A4 | 4 | 2.0 | $2.0 \times 10^{-3}$ |
| E4 | 2 | 0.9 | $6.6 \times 10^{-4}$ |

Example 5

Fyn SH3-Derived Polypeptides of the Invention Inhibit Protease Activity of Chymase The MR121 peptide fluorescence assay described below is based on the fact that MR121 forms a non-fluorescent ground state complex with tryptophan. In solution this formation occurs at millimolar concentrations of tryptophan. Here, the substrate peptide is labeled at one terminus with tryptophan and at the other terminus with the fluorophore MR121. In absence of protease activity, the substrate remains intact and the MR121 fluorescence is reduced by the high local concentration of tryptophan. If the substrate is cleaved by chymase, the MR121 fluorescence can be recorded. Therefore, the enzymatic reaction can be followed in a kinetic measurement detecting an increase of MR121 fluorescence during the reaction time. Calculating the slope in the linear range of the kinetic provides the value for the activity of the enzyme.

Methods:

The chymase fluorescent substrate kinetic assay was performed in triplicate at room temperature in 96-well microtiter plates (Costar). Each well contained 100 μl assay buffer (100 mM Hepes, pH 7.4; 0.01% Triton X-100, 80 μg/ml heparin) with 1 nM chymase, 1 μM unlabeled and 100 nM MR121 peptide (MR121-CAAPFW; Biosyntan GmbH, Berlin). Fyn SH3-derived (SEQ ID NOs: 2-9) were serially diluted in assay buffer (100 mM Hepes, pH 7.4; 0.01% Triton X-100, 80 μg/ml heparin) and added to the reaction solution as specified above. The enzymatic reaction was followed in a plate reader (Tecan Ultra, Tecan) at 612 nm excitation and 670 nm emission for 20 min in a kinetic measurement, detecting an increase of MR121 fluorescence during the reaction time. The slope in the linear range of the kinetic was calculated and $IC_{50}$ values of the Fyn SH3-derived polypeptides were calculated using a four parameter equation for curve fitting.

Results:

The titrated Fyn SH3-derived polypeptides showed dose-response curves demonstrating that they are potent inhibitors of chymase activity (see Table II).

TABLE II $IC_{50}$ values for inhibition of chymase activity.

| Clone | SEQ ID NO: | $IC_{50}$ (nM) |
|---|---|---|
| F12 | 5 | 5 |
| G2.3 | 6 | 1 |
| B5 | 3 | 11 |
| D7 | 7 | 6 |
| E3 | 9 | 78 |
| H2 | 8 | 18 |
| A4 | 4 | 4 |
| E4 | 2 | 2 |

Example 6

Crystal Structure of Chymase and Fyn SH3-Derived Polypeptides of the Invention Reveals Blockade of the Catalytic Site of Chymase by Fyn SH3-Derived Polypeptides of the Invention Three selected Fyn SH3-derived polypeptides, B5 (SEQ ID NO: 3), A4 (SEQ ID NO: 4) and E4 (SEQ ID NO: 2) were co-crystallized with chymase.

Methods:

Prior to crystallization experiments the Fyn SH3-derived polypeptides-chymase complexes were concentrated to 15 mg/ml. Crystallization screening against an INDEX screen (Hampton Research) was performed at 21° C. either in sitting drops by vapor diffusion or in microbatch experiments. Crystals appeared within one day and grew to their final size within 3 days after setup.

In all cases, data were processed with XDS (Kabsch W. (2010) Acta Crystallogr D Biol Crystallogr. (66) p. 125-132.) and scaled with SADABS (obtained from Bruker AXS). Refinement was performed with Refmac5 (Murshudov G N, et al. (1997). Acta Crystallogr D Biol Crystallogr., (53) p. 240-255) from the CCP4 suite (The CCP4 suite: programs for protein crystallography. (1994) Acta Crystallogr D Biol Crystallogr., (50), p. 760-763) or BUSTER (Bricogne G. (1993) Acta Crystallogr D Biol Crystallogr. (49), p. 37-60., Roversi P et al. (2000), Acta Crystallogr D Biol Crystallogr., (56) p. 1316-23, Blanc E. et al. (2004), Acta Crystallogr D Biol Crystallogr. (60) p. 2210-2221) and model building done with COOT (Emsley P et al. (2004) Acta Crystallogr D Biol Crystallogr., (60), p. 2126-2132).

Results:

Three different Fyn SH3 derived polypeptides binding to chymase (B5 (SEQ ID NO: 3) A4 (SEQ ID NO: 4) and E4 (SEQ ID NO: 2)) were co-crystallized with chymase.

TABLE III

The chymase-Fyn-SH3 derived polypeptide A4 (SEQ ID NO: 4) complex:

| | |
|---|---|
| Crystal parameters | SG19 59.630 92.792 116.256 90 90 90 |
| Resolution | 1.51 Å |
| Crystallization buffer | 0.1M Citric acid pH 3.5, 25% PEG 3'350 |
| Data collection and refinement | Data were collected on beam line X10SA (PXIII) at the Swiss Light Source (SLS) at wavelength 1.0 Å using a Pilatus pixel detector. For 101765 unique reflections to 1.51 Å resolution the merging R-factor on intensities was 6.5%. The final R-values were 18.9% (all data) and 21.5% (5% R-free). |

TABLE IV

Contacts between chymase and Fyn SH3-derived polypeptide A4 (SEQ ID NO: 4) All atom-atom contacts <3.5 Å are tabulated. Duplicates may occur as some residues have alternate conformations. The Fynomer numbering was chosen so that the first residue well visible in the first electron density is numbered 2. The chymase sequence is numbered serially from 1, so the catalytic serine is 182. 49 contacts found:

| CHYMASE | FYNOMER | DISTANCE |
|---|---|---|
| 201(SER) OG | 13(ALA) C | 3.45 |
| | 13(ALA) O | 3.31 |
| | 14(ASP) C | 3.06 |
| 200(ARG) CA | 14(ASP) O | 3.30 |
| 201(SER) N | 14(ASP) O | 2.90 |
| 201(SER) OG | 14(ASP) O | 3.33 |
| | 15(ARG) N | 3.19 |
| 199(GLY) O | 15(ARG) CA | 3.32 |
| 201(SER) OG | 15(ARG) C | 3.09 |
| | 15(ARG) O | 2.97 |
| 83(THR) O | 15(ARG) NH1 | 2.94 |
| 84(SER) O | 15(ARG) NH1 | 3.14 |
| 86(LEU) CD1 | 15(ARG) NH1 | 3.49 |
| 83(THR) O | 15(ARG) NH2 | 3.26 |
| 199(GLY) O | 16(TRP) N | 2.86 |
| 179(LYS) CE | 16(TRP) O | 3.37 |
| 199(GLY) N | 16(TRP) CD2 | 3.39 |
| 182(SER) OG | 16(TRP) NE1 | 3.32 |
| 199(GLY) CA | 16(TRP) CE3 | 3.42 |
| 199(GLY) N | 16(TRP) CE3 | 3.26 |
| 199(GLY) C | 16(TRP) CE3 | 3.45 |
| 199(GLY) CA | 16(TRP) CZ3 | 3.44 |
| 199(GLY) N | 16(TRP) CZ3 | 3.37 |
| 177(ALA) O | 16(TRP) CZ3 | 3.40 |
| | 16(TRP) CH2 | 3.45 |
| 77(ARG) NH1 | 31(ASP) OD2 | 2.82 |
| 77(ARG) NH2 | 33(SER) OG | 3.08 |
| | 34(PRO) CG | 3.50 |
| 82(ASN) CA | 35(PRO) O | 3.31 |
| 83(THR) N | 35(PRO) O | 2.84 |
| 83(THR) OG1 | 35(PRO) O | 3.46 |
| 81(TYR) O | 35(PRO) CD | 3.41 |
| 84(SER) OG | 36(GLY) CA | 3.48 |
| 83(THR) OG1 | 36(GLY) CA | 3.31 |
| | 36(GLY) C | 3.48 |
| 84(SER) OG | 37(ASP) N | 2.73 |
| | 37(ASP) CB | 3.42 |
| | 37(ASP) CG | 3.15 |
| | 37(ASP) OD1 | 3.43 |
| | 37(ASP) OD2 | 3.44 |
| 158(ARG) NH1 | 37(ASP) OD2 | 2.98 |
| 83(THR) OG1 | 38(TRP) N | 3.27 |
| | 38(TRP) O | 2.83 |
| 83(THR) O | 38(TRP) CD1 | 3.27 |
| 28(LYS) NZ | 40(GLU) OE2 | 2.78 |
| 22(THR) O | 42(ARG) NH1 | 3.31 |
| 81(TYR) OH | 51(TYR) CZ | 3.45 |
| 81(TYR) CZ | 51(TYR) OH | 3.49 |
| 81(TYR) OH | 51(TYR) OH | 2.59 |

It may be clearly seen that Trp16 of A4 inserts into the primary specificity pocket of chymase, which is thus inhibited.

TABLE VI

The chymase-Fyn SH3-derived polypeptide E4 (SEQ ID NO: 2) complex:

| | |
|---|---|
| Crystal parameters | SG19 58.998 59.855 89.711 90 90 90 |
| Resolution | 1.4 Å |
| Crystallization buffer | 0.1M Bis-Tris pH 5.5, 25% PEG 3'350 |
| Data collection and refinement | Data were collected on beam line X10SA (PXIII) at the Swiss Light Source (SLS) at wavelength 1.0 Å using a Pilatus pixel detector. |

TABLE VI-continued

The chymase-Fyn SH3-derived polypeptide E4 (SEQ ID NO: 2) complex:

For 63158 unique reflections to 1.4 Å resolution the merging R-factor on intensities was 9.9%. The final R-values were 18.6% (all data) and 20.5% (5% R-free).

TABLE VII

Contacts between chymase and E4 (SEQ ID NO: 2) All atom-atom contacts <3.5 Å are tabulated. Duplicates may occur as some residues have alternate conformations. The Fynomer numbering was chosen so that the first residue well visible in the first electron density is numbered 2. The chymase sequence is numbered serially from 1, so the catalytic serine is 182 (with closest contact 3.52 Å in this structure). In this structure the increased number of contacts occurs only because at the higher resolution it was possible to assign more alternative conformations to side chains, which are then counted twice. 75 contacts found:

| CHYMASE | FYNOMER | DISTANCE |
|---|---|---|
| 201(SER) OG | 13(ALA) C | 3.36 |
| | 13(ALA) O | 3.23 |
| | 14(THR) C | 3.15 |
| | 14(THR) O | 3.49 |
| 200(ARG) CA | 14(THR) O | 3.42 |
| 201(SER) N | 14(THR) O | 3.05 |
| 201(SER) OG | 15(ARG) N | 3.26 |
| | 15(ARG) N | 3.27 |
| 199(GLY) O | 15(ARG) CA | 3.24 |
| | 15(ARG) CA | 3.24 |
| 201(SER) OG | 15(ARG) C | 3.20 |
| 199(GLY) O | 15(ARG) C | 3.50 |
| 201(SER) OG | 15(ARG) C | 3.12 |
| 199(GLY) O | 15(ARG) C | 3.49 |
| 201(SER) OG | 15(ARG) O | 3.05 |
| | 15(ARG) O | 2.84 |
| 84(SER) O | 15(ARG) CZ | 3.43 |
| 83(THR) O | 15(ARG) NH1 | 3.33 |
| 84(SER) O | 15(ARG) NH1 | 2.80 |
| 84(SER) O | 15(ARG) NH1 | 3.04 |
| 86(LEU) CG | 15(ARG) NH1 | 3.35 |
| 84(SER) O | 15(ARG) NH1 | 2.66 |
| 84(SER) O | 15(ARG) NH1 | 2.85 |
| 83(THR) O | 15(ARG) NH2 | 3.08 |
| 84(SER) O | 15(ARG) NH2 | 3.35 |
| 84(SER) O | 15(ARG) NH2 | 3.38 |
| 159(ASP) OD2 | 15(ARG) NH2 | 2.71 |
| 199(GLY) O | 16(TRP) N | 2.83 |
| 179(LYS) NZ | 16(TRP) O | 2.82 |
| 179(LYS) CE | 16(TRP) O | 3.43 |
| 199(GLY) N | 16(TRP) CD2 | 3.43 |
| 178(PHE) CD1 | 16(TRP) CE3 | 3.44 |
| 199(GLY) N | 16(TRP) CE3 | 3.22 |
| 199(GLY) CA | 16(TRP) CE3 | 3.42 |
| 199(GLY) N | 16(TRP) CZ3 | 3.35 |
| 199(GLY) CA | 16(TRP) CZ3 | 3.44 |
| 177(ALA) O | 16(TRP) CZ3 | 3.44 |
| | 16(TRP) CH2 | 3.49 |
| 24(ASN) ND2 | 28(GLN) CB | 3.50 |
| 24(ASN) OD1 | 28(GLN) CG | 3.39 |
| 24(ASN) ND2 | 28(GLN) CG | 3.23 |
| | 28(GLN) CD | 3.40 |
| | 28(GLN) OE1 | 3.33 |
| 23(SER) OG | 30(LEU) O | 3.13 |
| 24(ASN) N | 30(LEU) CD2 | 3.39 |
| 24(ASN) N | 30(LEU) CD2 | 3.44 |
| 77(ARG) NH1 | 31(GLU) OE1 | 2.84 |
| | 31(GLU) OE2 | 3.42 |
| 77(ARG) NH2 | 31(GLU) OE2 | 2.96 |
| 83(THR) N | 34(PRO) O | 2.83 |
| 83(THR) OG1 | 34(PRO) O | 3.37 |

TABLE VII-continued

Contacts between chymase and E4 (SEQ ID NO: 2)
All atom-atom contacts <3.5 Å are tabulated.
Duplicates may occur as some residues have alternate
conformations. The Fynomer numbering was chosen
so that the first residue well visible in the first electron
density is numbered 2. The chymase sequence is
numbered serially from 1, so the catalytic serine is
182 (with closest contact 3.52 Å in this structure).
In this structure the increased number of contacts occurs
only because at the higher resolution it was possible
to assign more alternative conformations to side chains,
which are then counted twice.
75 contacts found:

| CHYMASE | FYNOMER | DISTANCE |
|---|---|---|
| 83(THR) CG2 | 34(PRO) O | 3.49 |
| 82(ASN) CA | 34(PRO) O | 3.32 |
| 84(SER) OG | 36(ASP) N | 3.48 |
|  | 36(ASP) CB | 3.39 |
| 83(THR) OG1 | 37(TRP) N | 3.17 |
|  | 37(TRP) C | 3.45 |
| 83(THR) CB | 37(TRP) O | 3.39 |
| 83(THR) OG1 | 37(TRP) O | 2.68 |
|  | 37(TRP) CB | 3.46 |
| 84(SER) OG | 37(TRP) CD1 | 3.43 |
| 28(LYS) CE | 39(GLU) OE2 | 3.49 |
| 28(LYS) NZ | 39(GLU) OE2 | 2.63 |
| 24(ASN) O | 41(ARG) NE | 3.05 |
| 24(ASN) O | 41(ARG) NE | 2.63 |
| 24(ASN) O | 41(ARG) CZ | 3.38 |
| 24(ASN) O | 41(ARG) CZ | 3.29 |
| 24(ASN) O | 41(ARG) NH2 | 2.86 |
| 24(ASN) O | 41(ARG) NH2 | 3.09 |
| 22(THR) OG1 | 41(ARG) NH2 | 2.95 |
| 26(PRO) O | 41(ARG) NH2 | 2.59 |
| 83(THR) CG2 | 50(TYR) CE1 | 3.41 |
| 81(TYR) OH | 50(TYR) CE2 | 3.37 |
|  | 50(TYR) CZ | 3.33 |
|  | 50(TYR) OH | 2.69 |

TABLE VIII

The chymase-Fyn SH3-derived polypeptide B5
(SEQ ID NO: 3) complex:

| | |
|---|---|
| Crystal parameters | SG19 56.937 64.124 174.987 90 90 90 |
| Resolution | 1.8 Å |
| Crystallization buffer | 0.15M DL-Malic acid pH 7.0, 20% PEG 3'350 |
| Data collection and refinement | Data were collected on beam line X10SA (PXIII) at the Swiss Light Source (SLS) at wavelength 1.0 Å using a Pilatus pixel detector. For 62210 unique reflections to 1.78 Å resolution the merging R-factor on intensities was 9.4%. The final R-values were 18.0% (all data) and 21.2% (5% R-free). |

TABLE IX

Contacts between chymase and B5 (SEQ ID NO: 3)
All atom-atom contacts <3.5 Å are tabulated. Duplicates
may occur as some residues have alternate conformations.
The Fynomer numbering was chosen so that the first residue
well visible in the first electron density is numbered 2. The
Chymase sequence is numbered serially from 1, so the
catalytic serine is 182. In this structure the increased number of
contacts occurs partly because Trp16 of B5 was assigned 2
alternative conformations and partly due to slight differences
in B5 Arg15.
67 contacts found:

| CHYMASE | FYNOMER | DISTANCE |
|---|---|---|
| 201(SER) OG | 13(ALA) C | 3.28 |
|  | 13(ALA) O | 3.34 |
|  | 13(ALA) CB | 3.33 |
|  | 14(THR) N | 3.43 |
|  | 14(THR) C | 3.11 |
| 200(ARG) CA | 14(THR) O | 3.45 |
| 201(SER) N | 14(THR) O | 2.96 |
| 201(SER) OG | 14(THR) O | 3.44 |
|  | 15(ARG) N | 3.18 |
| 199(GLY) O | 15(ARG) CA | 3.14 |
| 201(SER) OG | 15(ARG) C | 3.26 |
|  | 15(ARG) O | 3.17 |
| 198(TYR) OH | 15(ARG) NH1 | 3.43 |
| 198(TYR) CZ | 15(ARG) NH1 | 3.38 |
| 85(THR) O | 15(ARG) NH1 | 3.38 |
| 159(ASP) OD2 | 15(ARG) NH1 | 3.14 |
| 159(ASP) CG | 15(ARG) NH2 | 3.41 |
| 159(ASP) OD2 | 15(ARG) NH2 | 3.16 |
| 159(ASP) OD1 | 15(ARG) NH2 | 2.88 |
| 199(GLY) O | 16(TRP) N | 2.92 |
|  | 16(TRP) N | 2.94 |
| 179(LYS) NZ | 16(TRP) O | 2.82 |
|  | 16(TRP) O | 2.91 |
| 178(PHE) CD1 | 16(TRP) CD1 | 3.28 |
| 178(PHE) CE1 | 16(TRP) CD1 | 3.35 |
| 200(ARG) O | 16(TRP) CD1 | 3.15 |
| 199(GLY) C | 16(TRP) CD1 | 3.39 |
| 199(GLY) O | 16(TRP) CD1 | 3.37 |
| 199(GLY) N | 16(TRP) CD2 | 3.40 |
|  | 16(TRP) NE1 | 3.06 |
| 199(GLY) CA | 16(TRP) NE1 | 3.30 |
| 199(GLY) N | 16(TRP) CE2 | 3.34 |
|  | 16(TRP) CE3 | 3.19 |
| 199(GLY) CA | 16(TRP) CE3 | 3.36 |
| 178(PHE) CD1 | 16(TRP) CE3 | 3.43 |
| 177(ALA) O | 16(TRP) CZ3 | 3.29 |
| 199(GLY) N | 16(TRP) CZ3 | 3.26 |
| 199(GLY) CA | 16(TRP) CZ3 | 3.32 |
| 182(SER) OG | 16(TRP) CZ3 | 2.92 |
| 177(ALA) O | 16(TRP) CH2 | 3.41 |
| 182(SER) OG | 16(TRP) CH2 | 2.95 |
| 77(ARG) NH1 | 31(PRO) OD2 | 2.86 |
| 83(THR) N | 34(SER) O | 3.04 |
| 83(THR) OG1 | 34(SER) O | 3.44 |
| 83(THR) CG2 | 34(SER) O | 3.37 |
| 77(ARG) NH2 | 34(SER) CB | 3.44 |
| 77(ARG) CZ | 34(SER) OG | 3.36 |
| 77(ARG) NH1 | 34(SER) OG | 3.27 |
| 77(ARG) NH2 | 34(SER) OG | 2.67 |
| 83(THR) OG1 | 35(GLY) CA | 3.23 |
|  | 35(GLY) C | 3.30 |
| 84(SER) OG | 36(ASP) N | 3.35 |
| 83(THR) OG1 | 37(TRP) N | 3.41 |
|  | 37(TRP) C | 3.49 |
| 83(THR) CB | 37(TRP) O | 3.21 |
| 83(THR) OG1 | 37(TRP) O | 2.55 |
| 84(SER) OG | 37(TRP) CD1 | 3.48 |
| 28(LYS) NZ | 39(GLU) CD | 3.43 |
|  | 39(GLU) OE2 | 2.53 |
| 25(GLY) CA | 41(ARG) CZ | 3.33 |
| 26(PRO) O | 41(ARG) NH1 | 3.25 |
| 23(SER) O | 41(ARG) NH2 | 3.07 |
| 25(GLY) N | 41(ARG) NH2 | 3.27 |
| 25(GLY) CA | 41(ARG) NH2 | 3.38 |
| 81(TYR) OH | 50(TYR) CZ | 3.40 |
| 45(HIS) CB | 50(TYR) OH | 3.41 |
| 81(TYR) OH | 50(TYR) OH | 2.71 |

From the solved structures it can be seen that the main element for the interaction between the Fyn SH3-derived polypeptides and chymase are the sequence motif Arg15-Trp16 of the Fyn SH3-derived polypeptides, which confer to tight binding into the chymase active site. It is obvious that such a binding in the active site prevents the enzyme from being active, thus explaining the potent $IC_{50}$ values which have been determined in the enzymatic assay (Example 5).

Other indicated amino acids of the Fyn SH3-derived polypeptides make additional surface contacts with the 24 loop of chymase.

All six complex structures are very similar. The slight differences in the Fyn SH3-derived polypeptides-chymase orientation come from both the sequence differences and crystal packing and are approximately a rigid body rotation about Trp16 in the S1 pocket of chymase.

The presence of a Fyn SH3-derived polypeptide has only a minor influence on the overall conformation of chymase. The most pronounced change affects the 24 loop of chymase which seems to adapt slightly upon binding.

All resolved Fyn SH3-derived polypeptides adopt a typical SH3 domain fold.

The invention claimed is:

1. An isolated polypeptide binding to a chymase comprising the amino acid sequence selected from the group consisting of SEQ ID NO: 2, 3, 4, 5, 6, 7, 8, 9, 10, 11, 12, 13, 14, or 15.

2. The polypeptide of claim 1, wherein the polypeptide consists of the amino acid sequence selected from the group consisting of SEQ ID NOs: 2 to 15.

3. The polypeptide of claim 1, wherein the chymase comprises the amino acids sequence of SEQ ID NO: 16.

4. A fusion protein comprising the polypeptide of claim 1 fused to an $F_c$ domain of an antibody, an albumin binder, an albumin, an IgG binder, or antibody.

5. A fusion construct comprising the polypeptide of claim 1 fused to a pharmaceutically active compound, a diagnostically active compound and/or a component modulating serum half-life.

6. The fusion construct of claim 5, wherein the pharmaceutically active compound or diagnostically active compound is selected from the group consisting of
   (a) a fluorescent dye,
   (b) a photosentisizer,
   (c) a radionuclide,
   (d) a contrast agent for medical imaging,
   (e) a cytokine,
   (f) a toxic compound,
   (g) a chemokine,
   (h) pro-coagulant factor,
   (i) an enzyme for pro-drug activation, or
   (k) an angiotensin converting enzyme (ACE) inhibitor, a renin inhibitor, an antidiuretic hormone (ADH) inhibitor, an aldosteron inhibitor, or an angiotensin receptor blocker.

7. A method for treating an inflammatory condition, cardiovascular disease or cancer, wherein the inflammatory condition is selected from asthma and chronic obstructive pulmonary disease (COPD), wherein the cardiovascular disease is selected from cardiomyopathy, myocardial infarction, left ventricular hypertrophy, tachycardia-induced heart failure, vascular proliferation after balloon catheter injury, and wherein the cancer is uterine cervical carcinoma, comprising administering a pharmaceutical composition comprising the polypeptide of claim 1.

8. A method for treating organ damage, wherein the organ damage is induced by aortic aneurysm, diabetic retinopathy, fibrosis, ulcerative colitis or another inflammatory disease comprising administering a pharmaceutical composition comprising the polypeptide of claim 1.

* * * * *

SEQUENCE LISTING

```
<160> NUMBER OF SEQ ID NOS: 17

<210> SEQ ID NO 1
<211> LENGTH: 65
<212> TYPE: PRT
<213> ORGANISM: Artificial sequence
<220> FEATURE:
<223> OTHER INFORMATION: SH3 domain of the Fyn Kinase
<220> FEATURE:
<221> NAME/KEY: variant
<222> LOCATION: 12
<223> OTHER INFORMATION: /replace=Cys, Asp, Glu, Phe, Gly, His, Ile,
      Lys, Leu, Met, Asn, Pro, Gln, Arg, Ser, Thr, Val, Trp, Tyr
<220> FEATURE:
<221> NAME/KEY: variant
<222> LOCATION: 14
<223> OTHER INFORMATION: /replace=Cys, Asp, Glu, Phe, Gly, His, Ile,
      Lys, Leu, Met, Asn, Pro, Gln, Arg, Ser, Thr, Val, Trp, Tyr
<220> FEATURE:
<221> NAME/KEY: variant
<222> LOCATION: 15
<223> OTHER INFORMATION: /replace=Cys, Asp, Glu, Phe, Gly, His, Ile,
      Lys, Leu, Met, Asn, Pro, Gln, Arg, Ser, Thr, Val, Trp, Tyr
<220> FEATURE:
<221> NAME/KEY: variant
<222> LOCATION: 16
<223> OTHER INFORMATION: /replace=Cys, Asp, Glu, Phe, Gly, His, Ile,
      Lys, Leu, Met, Asn, Pro, Gln, Arg, Ser, Thr, Val, Trp, Tyr
<220> FEATURE:
<221> NAME/KEY: variant
<222> LOCATION: 17
<223> OTHER INFORMATION: /replace=Cys, Asp, Glu, Phe, Gly, His, Ile,
      Lys, Leu, Met, Asn, Pro, Gln, Arg, Ser, Thr, Val, Trp, Tyr
<220> FEATURE:
<221> NAME/KEY: variant
<222> LOCATION: 18
<223> OTHER INFORMATION: /replace=Cys, Asp, Glu, Phe, Gly, His, Ile,
      Lys, Leu, Met, Asn, Pro, Gln, Arg, Ser, Thr, Val, Trp, Tyr
<220> FEATURE:
<221> NAME/KEY: variant
<222> LOCATION: 31
<223> OTHER INFORMATION: /replace=Cys, Asp, Glu, Phe, Gly, His, Ile,
      Lys, Leu, Met, Asn, Pro, Gln, Arg, Ser, Thr, Val, Trp, Tyr
<220> FEATURE:
<221> NAME/KEY: variant
<222> LOCATION: 32
<223> OTHER INFORMATION: /replace=Cys, Asp, Glu, Phe, Gly, His, Ile,
      Lys, Leu, Met, Asn, Pro, Gln, Arg, Ser, Thr, Val, Trp, Tyr
<220> FEATURE:
<221> NAME/KEY: variant
<222> LOCATION: 33
<223> OTHER INFORMATION: /replace=Cys, Asp, Glu, Phe, Gly, His, Ile,
      Lys, Leu, Met, Asn, Pro, Gln, Arg, Ser, Thr, Val, Trp, Tyr
<220> FEATURE:
<221> NAME/KEY: variant
<222> LOCATION: 34
<223> OTHER INFORMATION: /replace=Cys, Asp, Glu, Phe, Gly, His, Ile,
      Lys, Leu, Met, Asn, Pro, Gln, Arg, Ser, Thr, Val, Trp, Tyr
<220> FEATURE:
<221> NAME/KEY: variant
<222> LOCATION: 35
<223> OTHER INFORMATION: /replace=Cys, Asp, Glu, Phe, Gly, His, Ile,
      Lys, Leu, Met, Asn, Pro, Gln, Arg, Ser, Thr, Val, Trp, Tyr
```

```
<220> FEATURE:
<221> NAME/KEY: variant
<222> LOCATION: 36
<223> OTHER INFORMATION: /replace=Cys, Asp, Glu, Phe, Gly, His, Ile,
      Lys, Leu, Met, Asn, Pro, Gln, Arg, Ser, Thr, Val, Trp, Tyr
<220> FEATURE:
<221> NAME/KEY: variant
<222> LOCATION: 38
<223> OTHER INFORMATION: /replace=Cys, Asp, Glu, Phe, Gly, His, Ile,
      Lys, Leu, Met, Asn, Pro, Gln, Arg, Ser, Thr, Val, Trp, Tyr
<220> FEATURE:
<221> NAME/KEY: variant
<222> LOCATION: 39
<223> OTHER INFORMATION: /replace=Cys, Asp, Glu, Phe, Gly, His, Ile,
      Lys, Leu, Met, Asn, Pro, Gln, Arg, Ser, Thr, Val, Trp, Tyr

<400> SEQUENCE: 1

Gly Val Thr Leu Phe Val Ala Leu Tyr Asp Tyr Ala Ala Ala Ala
1               5                   10                  15

Ala Ala Leu Ser Phe His Lys Gly Glu Lys Phe Gln Ile Leu Ala Ala
                20                  25                  30

Ala Ala Ala Ala Gly Ala Ala Trp Glu Ala Arg Ser Leu Thr Thr Gly
            35                  40                  45

Glu Thr Gly Tyr Ile Pro Ser Asn Tyr Val Ala Pro Val Asp Ser Ile
    50                  55                  60

Gln
65

<210> SEQ ID NO 2
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 2

Gly Val Thr Leu Phe Val Ala Leu Tyr Asp Tyr Asn Ala Thr Arg Trp
1               5                   10                  15

Thr Asp Leu Ser Phe His Lys Gly Glu Lys Phe Gln Ile Leu Glu Phe
                20                  25                  30

Gly Pro Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
    50                  55                  60

<210> SEQ ID NO 3
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 3

Gly Val Thr Leu Phe Val Ala Leu Tyr Asp Tyr Asn Ala Thr Arg Trp
1               5                   10                  15

Thr Asp Leu Ser Phe His Lys Gly Glu Lys Phe Gln Ile Leu Asp Gly
                20                  25                  30

Asp Ser Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
    50                  55                  60

<210> SEQ ID NO 4
```

-continued

```
<211> LENGTH: 64
<212> TYPE: PRT
<213> ORGANISM: Artificial sequence
<220> FEATURE:
<223> OTHER INFORMATION: SH3 domain of the Fyn Kinase

<400> SEQUENCE: 4

Gly Val Thr Leu Phe Val Ala Leu Tyr Asp Tyr Gln Ala Asp Arg Trp
1               5                   10                  15

Thr Asp Leu Ser Phe His Lys Gly Glu Lys Phe Gln Ile Leu Asp Ala
            20                  25                  30

Ser Pro Pro Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 5
<211> LENGTH: 65
<212> TYPE: PRT
<213> ORGANISM: Artificial sequence
<220> FEATURE:
<223> OTHER INFORMATION: SH3 domain of the Fyn Kinase

<400> SEQUENCE: 5

Gly Val Thr Leu Phe Val Ala Leu Tyr Asp Tyr Arg Ala Glu Arg Ser
1               5                   10                  15

Thr Asp Leu Ser Phe His Lys Gly Glu Lys Phe Gln Ile Leu Asp Met
            20                  25                  30

Thr Val Pro Asn Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 6
<211> LENGTH: 65
<212> TYPE: PRT
<213> ORGANISM: Artificial sequence
<220> FEATURE:
<223> OTHER INFORMATION: SH3 domain of the Fyn Kinase

<400> SEQUENCE: 6

Gly Val Thr Leu Phe Val Ala Leu Tyr Asp Tyr Asn Ala Thr Arg Trp
1               5                   10                  15

Thr Asp Leu Ser Phe His Lys Gly Glu Lys Phe Gln Ile Leu Asp Trp
            20                  25                  30

Thr Thr Ala Asn Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 7
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 7
```

```
Gly Val Thr Leu Phe Val Ala Leu Tyr Asp Tyr Gln Ala Asp Arg Trp
1               5                   10                  15

Thr Asp Leu Ser Phe His Lys Gly Glu Lys Phe Gln Ile Leu Ser Phe
                20                  25                  30

His Val Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
        50                  55                  60
```

<210> SEQ ID NO 8
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 8

```
Gly Val Thr Leu Phe Val Ala Leu Tyr Asp Tyr Gln Ala Asp Arg Trp
1               5                   10                  15

Thr Asp Leu Ser Phe His Lys Gly Glu Lys Phe Gln Ile Leu Arg Phe
                20                  25                  30

Asp Ile Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
        50                  55                  60
```

<210> SEQ ID NO 9
<211> LENGTH: 64
<212> TYPE: PRT
<213> ORGANISM: Artificial sequence
<220> FEATURE:
<223> OTHER INFORMATION: SH3 domain of the Fyn Kinase

<400> SEQUENCE: 9

```
Gly Val Thr Leu Phe Val Ala Leu Tyr Asp Tyr Gln Ala Asp Arg Trp
1               5                   10                  15

Thr Asp Leu Ser Phe His Lys Gly Glu Lys Phe Gln Ile Leu Asn Ala
                20                  25                  30

Ser Gly Pro Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60
```

<210> SEQ ID NO 10
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 10

```
Gly Val Thr Leu Phe Val Ala Leu Tyr Asp Tyr Glu Ala Gln Thr Trp
1               5                   10                  15

His Asp Leu Ser Phe His Lys Gly Glu Lys Phe Gln Ile Leu Asn Ser
                20                  25                  30

Ser Glu Gly Glu Tyr Trp Glu Ala Arg Ser Leu Thr Thr Gly Glu Thr
            35                  40                  45

Gly Leu Ile Pro Ser Asn Tyr Val Ala Pro Val Asp Ser Ile Gln
        50                  55                  60
```

<210> SEQ ID NO 11
<211> LENGTH: 65
<212> TYPE: PRT
<213> ORGANISM: Artificial sequence
<220> FEATURE:
<223> OTHER INFORMATION: SH3 domain of the Fyn Kinase

<400> SEQUENCE: 11

Gly Val Thr Leu Phe Val Ala Leu Tyr Asp Tyr Lys Ala Gln Arg Trp
1               5                   10                  15

Thr Asp Leu Ser Phe His Lys Gly Glu Lys Phe Gln Ile Leu Gln Ala
            20                  25                  30

His Gln Lys Thr Gly Asp Trp Trp Glu Ala Arg Ser Leu Thr Thr Gly
        35                  40                  45

Glu Thr Gly Leu Ile Pro Ser Asn Tyr Val Ala Pro Val Asp Ser Ile
    50                  55                  60

Gln
65

<210> SEQ ID NO 12
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 12

Gly Val Thr Leu Phe Val Ala Leu Tyr Asp Tyr Glu Ala Leu His Trp
1               5                   10                  15

His Gln Leu Ser Phe His Lys Gly Glu Lys Ser Gln Ile Leu Asn Ser
            20                  25                  30

Ser Glu Gly Thr Tyr Trp Glu Ala Arg Ser Leu Thr Thr Gly Glu Thr
        35                  40                  45

Gly Trp Ile Pro Ser Asn Tyr Val Ala Pro Gly Asp Ser Ile Gln
    50                  55                  60

<210> SEQ ID NO 13
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 13

Gly Val Thr Leu Phe Val Ala Leu Tyr Asp Tyr Lys Ala Gln Arg Trp
1               5                   10                  15

Leu Asp Leu Ser Phe His Glu Gly Glu Lys Phe Gln Ile Leu Ser Thr
            20                  25                  30

Asp Ser Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 14
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 14

```
Gly Val Thr Leu Phe Val Ala Leu Tyr Asp Tyr Glu Ala Pro Thr Trp
1               5                   10                  15

Leu His Leu Ser Phe His Lys Gly Glu Lys Phe Gln Ile Leu Asn Ser
            20                  25                  30

Ser Glu Gly Pro Trp Trp Glu Ala Arg Ser Leu Thr Thr Gly Glu Thr
        35                  40                  45

Gly Phe Ile Pro Ser Asn Tyr Val Ala Pro Val Asp Ser Ile Gln
    50                  55                  60
```

<210> SEQ ID NO 15
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 15

```
Gly Val Thr Leu Phe Val Ala Leu Tyr Asp Tyr Glu Ala Ala Asn Trp
1               5                   10                  15

Phe Gln Leu Ser Phe His Lys Gly Glu Lys Phe Gln Ile Leu Asn Ser
            20                  25                  30

Ser Glu Gly Pro Leu Trp Glu Ala Arg Ser Leu Thr Thr Gly Glu Thr
        35                  40                  45

Gly Gly Ile Pro Ser Asn Tyr Val Ala Pro Val Asp Ser Ile Gln
    50                  55                  60
```

<210> SEQ ID NO 16
<211> LENGTH: 226
<212> TYPE: PRT
<213> ORGANISM: Homo sapiens

<400> SEQUENCE: 16

```
Ile Ile Gly Gly Thr Glu Cys Lys Pro His Ser Arg Pro Tyr Met Ala
1               5                   10                  15

Tyr Leu Glu Ile Val Thr Ser Asn Gly Pro Ser Lys Phe Cys Gly Gly
            20                  25                  30

Phe Leu Ile Arg Arg Asn Phe Val Leu Thr Ala Ala His Cys Ala Gly
        35                  40                  45

Arg Ser Ile Thr Val Thr Leu Gly Ala His Asn Ile Thr Glu Glu Glu
    50                  55                  60

Asp Thr Trp Gln Lys Leu Glu Val Ile Lys Gln Phe Arg His Pro Lys
65              70                  75                  80

Tyr Asn Thr Ser Thr Leu His His Asp Ile Met Leu Leu Lys Leu Lys
            85                  90                  95

Glu Lys Ala Ser Leu Thr Leu Ala Val Gly Thr Leu Pro Phe Pro Ser
        100                 105                 110

Gln Phe Asn Phe Val Pro Pro Gly Arg Met Cys Arg Val Ala Gly Trp
    115                 120                 125

Gly Arg Thr Gly Val Leu Lys Pro Gly Ser Asp Thr Leu Gln Glu Val
130                 135                 140

Lys Leu Arg Leu Met Asp Pro Gln Ala Cys Ser His Phe Arg Asp Phe
145                 150                 155                 160

Asp His Asn Leu Gln Leu Cys Val Gly Asn Pro Arg Lys Thr Lys Ser
            165                 170                 175

Ala Phe Lys Gly Asp Ser Gly Gly Pro Leu Leu Cys Ala Gly Val Ala
        180                 185                 190

Gln Gly Ile Val Ser Tyr Gly Arg Ser Asp Ala Lys Pro Pro Ala Val
```

```
                     195                 200                 205
Phe Thr Arg Ile Ser His Tyr Arg Pro Trp Ile Asn Gln Ile Leu Gln
            210                 215                 220

Ala Asn
225

<210> SEQ ID NO 17
<211> LENGTH: 63
<212> TYPE: PRT
<213> ORGANISM: Homo sapiens

<400> SEQUENCE: 17

Gly Val Thr Leu Phe Val Ala Leu Tyr Asp Tyr Glu Ala Arg Thr Glu
1               5                   10                  15

Asp Asp Leu Ser Phe His Lys Gly Glu Lys Phe Gln Ile Leu Asn Ser
            20                  25                  30

Ser Glu Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
        50                  55                  60
```